United States Patent
Bottcher et al.

(10) Patent No.: US 9,328,065 B2
(45) Date of Patent: May 3, 2016

(54) NITROGEN-CONTAINING INORGANIC CARRIER MATERIALS

(71) Applicant: LANXESS Deutschland GmbH, Cologne (DE)

(72) Inventors: Andreas Bottcher, Cologne (DE); Hermann Uhr, Leverkusen (DE)

(73) Assignee: LANXESS Deutschland GmbH, Cologne (DE)

( * ) Notice: Subject to any disclaimer, the term of this patent is extended or adjusted under 35 U.S.C. 154(b) by 20 days.

(21) Appl. No.: 14/558,964

(22) Filed: Dec. 3, 2014

(65) Prior Publication Data

US 2015/0087700 A1 Mar. 26, 2015

Related U.S. Application Data

(62) Division of application No. 13/377,614, filed as application No. PCT/EP2010/058259 on Jun. 11, 2010, now abandoned.

(30) Foreign Application Priority Data

Jun. 12, 2009 (EP) ..................................... 09162601

(51) Int. Cl.
*C07C 269/08* (2006.01)
*A01N 47/12* (2006.01)

(52) U.S. Cl.
CPC .............. *C07C 269/08* (2013.01); *A01N 47/12* (2013.01)

(58) Field of Classification Search
CPC ... A01N 47/12; A01N 25/22; A01N 2300/00; C07C 269/08
See application file for complete search history.

(56) References Cited

U.S. PATENT DOCUMENTS

| | | | |
|---|---|---|---|
| 7,098,279 B2 * | 8/2006 | Maandi et al. ................. | 526/195 |
| 2003/0109598 A1 * | 6/2003 | Winkowski et al. .......... | 523/122 |
| 2007/0036832 A1 * | 2/2007 | Williams ............... | A01N 47/12 |
| | | | 424/405 |

FOREIGN PATENT DOCUMENTS

CA 2175480 * 5/1995

* cited by examiner

*Primary Examiner* — Johann R Richter
*Assistant Examiner* — Genevieve S Alley

(57) ABSTRACT

The invention relates to nitrogen-containing inorganic carrier materials, more particularly to inorganic carrier materials containing organically bonded nitrogen, to their preparation and also to their use for stabilizing iodine-containing compounds, and also to binder formulations comprising them and to the use thereof for protecting industrial materials.

18 Claims, No Drawings

NITROGEN-CONTAINING INORGANIC CARRIER MATERIALS

CROSS REFERENCE TO RELATED PATENT APPLICATIONS

This application is a divisional of pending U.S. patent application Ser. No. 13/377,614, filed Mar. 27, 2012, with the same title, which claims the right of priority under 35 U.S.C. §119 (a)-(d) and 35 U.S.C. §365 of International Application No. PCT/EP2010/58259, filed Jun. 11, 2010, which was published in German as International Patent Publication No. WO 2010/142795 A1 on Dec. 16, 2010, which is entitled to the right of priority of European Patent Application No. EP 09162601 filed on Jun. 12, 2009.

The invention relates to carrier materials containing nitrogen, especially organically bonded nitrogen, to the preparation thereof and to the use thereof for stabilizing iodine-containing compounds, and to binder formulations comprising them and to the use thereof for the protection of industrial materials.

Iodine-containing biocides are used for providing industrial materials, coating materials being an example, with protection from infestation, decomposition, destruction and visual alteration by fungi, bacteria and algae, preferentially by fungi. Furthermore, iodine-containing biocides, both alone and in combination with biocides from other classes of active ingredient, are used as components of biocidally active materials protection compositions such as wood preservatives. Besides iodoalkynyl compounds, the active ingredients used here include compounds in which one or more atoms of iodine are attached to double-bond systems, but also to singly bonded carbon atoms.

A behaviour common to many iodine-containing biocides is that on exposure to light even in bulk or as a component of an industrial material (coating material, for example) they lead to yellowing with breakdown of the active compound. This feature hinders or prevents the use of iodine-containing biocides in materials having such sensitivity, such as in light-coloured or white coating materials, for example. For the IPBC, these instability qualities are described in WO00/16628 for example.

Many iodine-containing biocides, particularly iodoalkynyl compounds, are destroyed with particular rapidity by metal compounds. This fact prevents iodoalkynyl compounds, for example, from being used in solvent-based coating materials, such as paints, varnishes and stains, for example, or in biocidal preservatives, such as wood preservative primers, wood preservative impregnation systems and wood preservative stains, for example, since these alkyd-based coating and preservation systems are regularly equipped with metal compounds. In such systems, transition metal compounds, examples being cobalt, lead, manganese and vanadium octoates, function as dryers (siccatives) for the alkyd resin-containing binder system. Moreover, transition metal compounds are also used as pigments, and in some cases have destructive properties comparable with the siccatives.

In the solvent-based systems referred to above, there are, in addition to the dryers, a series of further ingredients which, to different degrees, lead to breakdown of iodine-containing biocides. Whereas the destabilizing effect is still relatively weak with the solvents that are customarily used, the other customary components of a paint formulation, such as process additives, plasticizers, colour pigments, anti-settling agents, thixotropic agents, corrosion inhibitors, anti-skinning agents and binders, for example, exhibit more or less strongly pronounced destabilizing effects.

As well as in the solvent-based systems described above, problems also attend the use of iodine-containing biocides in certain water-based industrial materials (e.g. coating materials and preservatives such as wood preservative stains and primers). Where the film formation and film hardening of a water-based coating material is based, for example, on the oxidative crosslinking of water-soluble or emulsified alkyd resins, transition metal compounds are employed as siccatives in these systems as well, and their use is accompanied by destruction of the iodine-containing biocides present.

There are already methods known for preventing the degradation of halopropargyl compounds in transition-metal-containing, solvent-based alkyd-resin paints. WO 98/22543, for example, describes the addition of chelating reagents.

Also known are transition-metal-containing, solvent-based alkyd-resin paints where halopropargyl compounds are stabilized by means of organic epoxides (cf. WO 00/16628).

Moreover, there are already descriptions of methods of suppressing the light-induced degradation of active antifungal compounds, such as iodopropargyl butylcarbamate, by addition of tetraalkylpiperidine compounds and/or UV absorbers (cf. EP-A 0083308).

According to WO 2007/028527, iodine-containing biocides are stabilized with 2-(2-hydroxy-phenyl)benzotriazoles.

Addition of epoxy compounds is said to reduce the discoloration of iodoalkyne compounds, such as IPBC (cf. U.S. Pat. No. 4,276,211 and U.S. Pat. No. 4,297,258).

Furthermore, there are descriptions of synergistic mixtures of epoxides with UV absorbers (cf. WO 99/29176) and with benzylidene camphor derivatives (cf. U.S. Pat. No. 6,472,424), which likewise exhibit reduced yellowing.

WO 2007/101549, moreover, describes the stabilization of iodine-containing biocides by means of azole compounds.

The stabilizing action of the aforementioned stabilizers, however, is not always sufficient, and carries performance disadvantages. Thus, in particular, the drying times of the paints are markedly prolonged, and in many cases this is unacceptable to the user. Moreover, the inhibition of discoloration is not always sufficient.

Surprisingly, it has now been found that the use of nitrogen-containing inorganic carrier materials makes it possible to provide iodine-containing biocides, particularly in solvent-based and water-based systems, with protection against both chemical and light-induced degradation, and hence to prevent the above-described disadvantages of unstabilized iodine-containing compounds, such as alterations to colour and loss of active compound/activity. It has been found, moreover, that using nitrogen-containing carrier materials to stabilize iodine-containing biocides in the aforementioned systems engenders no performance disadvantages, such as the prolongation of the drying time of a coating system, for example.

Aziridine compounds are employed, for example, in US2004/0077783 A1 as part of polymerization initiators which as further ingredients comprise organoborane compounds, carrier materials and optionally fillers. The latter are present as a concomitant of the preparation process, but as mixtures with the other components, and not as carrier materials surface-modified with aziridine.

Through the use of inorganic carrier materials containing nitrogen, the specific properties of liquid, iodine-containing formulations, e.g. solutions and dispersions, such as, for example, low concentration and hence unnecessary transport of solvent, are improved still further. As compared with iodine-containing solutions, this form possesses, in particular, stability advantages, particularly in storage, preferably at elevated temperatures.

In one aspect, therefore, the invention relates to nitrogen-containing inorganic carrier materials. Nitrogen-containing inorganic carrier materials in the context of the invention are inorganic carrier materials comprising at least one absorptively or covalently bonded, nitrogen-containing compound.

For clarification it is noted that the term "nitrogen-containing inorganic carrier materials" also encompasses those inorganic carrier materials which comprise in each case absorptively and covalently bonded nitrogen-containing compounds, and also those inorganic carrier materials comprising different nitrogen-containing compounds, of which at least one is covalently bonded and at least one is adsorptively bonded.

In one preferred embodiment, the nitrogen-containing inorganic carrier materials comprise the nitrogen in organically bonded form, where, for the purposes of the invention, organically bonded nitrogen means nitrogen which has at least one bond to a carbon atom, with the exception of cyanide and isocyanate ions and of prussic acid and isocyanic acid.

For clarification and in order to simplify the nomenclature, it is noted that the term "nitrogen-containing inorganic carrier materials" also encompasses those materials in which the inorganic carrier materials comprise covalently bonded nitrogen-containing compounds in which the nitrogen is organically bonded.

The nitrogen-containing inorganic carrier materials of the invention are preferably solid at room temperature.

The nitrogen-containing inorganic carrier materials of the invention are prepared preferably by reaction of inorganic carrier materials with at least one nitrogen-containing compound, the nitrogen-containing compounds preferably being organic compounds.

In one preferred embodiment, nitrogen-containing inorganic carrier materials of the invention have a nitrogen content of 0.05% to 10% by weight, preferably of 0.1% to 10% by weight. Unless indicated otherwise, nitrogen contents are determined quantitatively by elemental analysis using a combustion method.

Since, in the reaction of nitrogen-containing compounds with the inorganic carrier materials, especially in those cases in which covalent bonds are formed as well, the reaction mechanisms are frequently opaque, multilayered and not amenable to full structural elucidation, the invention also encompasses nitrogen-containing inorganic carrier materials comprising compounds obtainable through reaction of inorganic carrier materials with nitrogen-containing compounds, where the preference ranges specified for nitrogen-containing inorganic carrier materials in general apply in the same way Suitable inorganic carrier materials are for example and preferably silicas such as, for example, precipitated silicas, such as silica gels, mesoporous silicates, xerogels, aerogels, fumed silicas, silicas modified with organic, inorganic or organometallic radicals, examples being dichlorodialkylsilane-modified silicas, kieselguhr, porosils, e.g. zeosils, clathrasils or dealuminated zeolites, aluminosilicates, zeolites, natural or synthetic tectosilicates, natural silicates such as, e.g., vermiculite, mica or pyrogenic metal oxides, for example $TiO_2$, including pyrogenic mixed metal oxides.

Preference is given to fumed silicas, more particularly hydrophilic or hydrophobic ones, as for example those in commerce under the name Aerosil® from Evonik-Degussa, the product Aerosil® 200 being particularly preferred.

It is also preferred for the inorganic carrier material, in the event that the heterocyclic 3-membered-ring compound is an aziridine, does not comprise any organoborane.

Likewise preferred are hydrophilic or hydrophobic precipitated silicas, more particularly hydrophilic or hydrophobic ones, examples being those in commerce under the name Sipernat® from Evonik-Degussa. In this case, the products Sipernat®22S and Sipernat®50S are particularly preferred.

The nitrogen-containing inorganic carrier materials of the invention preferably have a particle size of 0.001 to 1000 μm, more particularly of 0.005 to 500 μm.

The nitrogen-containing inorganic carrier materials of the invention are notable preferably for the capacity to absorb liquids, measured by means of their DBP absorbency (DBP=dibutyl phthalate; see DIN 53601 and ISO 4656) in grams per 100 g of carrier material. The DBP absorbency of the carrier materials of the invention is preferably 0.1 to 800 g/100 g. more preferably 1 to 500 g/100 g of carrier material.

The nitrogen-containing inorganic carrier materials of the invention preferably possess a specific surface area [$m^2/g$], determined in a method based on that of Brunauer, Emmett and Teller (BET surface area; J. Am. Chem. Soc. 60, 309 (1938)), in accordance with ISO 5794/1 (Annex D), of 1 to 1200 $m^2/g$, more preferably of 50 to 900 $m^2/g$.

Examples of suitable nitrogen-containing compounds are those in which the nitrogen is organically bonded.

Such compounds include, for example, mononitrogen compounds and polynitrogen compounds Mononitrogen compounds are, for example, those of the formula (Ia)

$$R^1R^2R^3N \qquad (Ia)$$

in which $R^1$, $R^2$ and $R^3$ each independently of one another are hydrogen, alkyl, alkenyl or aryl or in pairs together form a 3- to 7-membered N-heterocyclic, aliphatic, unsaturated or aromatic ring, the radicals alkyl, alkenyl or aryl or the 3- to 7-membered N-heterocyclic, aliphatic, unsaturated or aromatic ring being either unsubstituted or substituted one or more times by radicals selected from the group consisting of hydroxyl, fluoro, chloro, bromo, iodo, carboxyl, alkylsulphonyl, arylsulphonyl, nitrile and isonitrile, but at least one of the radicals $R^1$, $R^2$ and $R^3$ is not hydrogen.

Compounds of the formula (Ia) are, for example, aminoethanol and (2-[(1-methylpropyl)-amino]ethanol.

Polynitrogen compounds are, for example, polyamines such as, for example, aliphatic diamines such as, for example, ethylenediamine, 1,2- and 1,3-propanediamine, 2-methyl-1,2-propanediamine, 2,2-dimethyl-1,3-propanediamine, 1,3- and 1,4-butane-diamine, 1,3- and 1,5-pentanediamine, 1,6-hexanediamine, 2,2,4- and 2,4,4-trimethylhexamethylenediamine and mixtures thereof, 1,7-heptanediamine, 1,8-octanediamine, 1,9-nonanediamine, 1,10-decanediamine, 1,11-undecanediamine, 1,12-dodecanediamine, methylbis(3-aminopropyl)amine, 1,5-diamino-2-methylpentane (MPMD), 1,3-diaminopentane (DAMP), 2,5-dimethyl-1,6-hexamethylenediamine, cycloaliphatic polyamines such as, for example, 1,3- and 1,4-diaminocyclohexane, bis(4-aminocyclohexyl)methane, bis(4-amino-3-methylcyclohexyl)methane, bis(4-amino-3-ethylcyclohexyl)methane, 2-methylpentamethylenediamine, bis(4-amino-3,5-dimethylcyclohexyl)methane, 1-amino-3-aminomethyl-3,5,5-trimethylcyclohexane (=isophoronediamine or IPDA), 2- and 4-methyl-1,3-diaminocyclohexane and mixtures thereof, 1,3- and 1,4-bis(aminomethyl)cyclohexane, 1-cyclohexylamino-3-aminopropane, 2,5(2,6)-bis(aminomethyl)bicyclo[2.2.1]heptane (NBDA, manufactured by Mitsui Chemicals), 3(4),8(9)-bis(aminomethyl)tricyclo[5.2.1.0$^{2.6}$]decane, 1,4-diamino-2,2,6-trimethylcyclohexane (TMCDA), 3,9-bis(3-aminopropyl)-2,4,8,
10-tetraoxaspiro[5.5]undecane, piperazine, 1-(2-aminoethyl)piperazine, aromatic polyamines such as 1,3- and 1,4-xylylenediamine;

aliphatic amines with a functionality of two or more which as well as one or more primary amino groups carry more than one secondary amino group, such as diethylenetriamine (DETA), triethylenetetramine (TETA), tetraethylenepentamine (TEPA), pentaethylenehexamine and higher homologues of linear polyethylenamines, N,N'-bis(3-aminopropyl)ethylenediamine, polyvinylamines, and also polyethylenimines with different degrees of polymerization (molar mass range 500 to 1 000 000 g/mol), as are obtainable, for example, under the trade name Lupasol® from BASF in pure form or as aqueous solutions, these polyethylenimines containing not only primary and secondary but also tertiary amino groups;

polyamidoamines aliphatic polyamines containing ether groups, such as bis (2-aminoethyl) ether, 4,7-dioxadecane-1,10-diamine, 4,9-dioxadodecane-1,12-diamine and higher oligomers thereof, polyoxyalkylene-polyamines having two or three amino groups, as obtainable for example under the name Jeffamine® (from Huntsman Chemicals), under the name Polyetheramin (from BASF) or under the name PC Amine® (from Nitroil), and also mixtures of the aforementioned polyamines.

Particularly suitable nitrogen-containing compounds are aziridines.

Aziridines contemplated are those which comprise one or more aziridine groups.

Preferred aziridines are, for example to aziridine compounds of the formula (I)

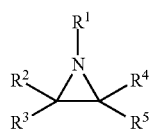
(I)

where $R^1$ is hydrogen, alkyl or cycloalkyl, each of which are unsubstituted or substituted and/or mono- or polyethylenically unsaturated, or in each case substituted or unsubstituted fullerenyl, aryl, alkoxy, alkoxycarbonyl, arylcarbonyl, alkanoyl, carbamoyl or oxomethylene, $R^2$, $R^3$, $R^4$ and $R^5$, independently of one another have the same definition as $R^1$ and additionally independently are halogen, hydroxyl, carboxyl, alkylsulphonyl, arylsulphonyl, nitrile, isonitrile or the radicals $R^2$ and $R^4$ or $R^3$ and $R^5$, together with the carbon atoms to which they are attached, form a 5- to 10-membered carbocyclic ring which is unsubstituted or substituted and/or mono- or polyethylenically unsaturated.

Monofunctional aziridines of the formula (I) that are contemplated are, for example, those in which $R^2$ and $R^4$ or $R^3$ and $R^5$, together with the carbon atoms to which they are attached, form a 5- to 10-membered carbocyclic ring which is unsubstituted or substituted and/or mono- or polyethylenically unsaturated.

These are, more particularly, those of the formula (II)

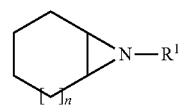
(II)

where the carbocyclic ring is unsubstituted or substituted by one or more substituents selected from the group consisting of halogen, hydroxyl, oxo, carboxyl, alkylsulphonyl, arylsulphonyl, nitrile, isonitrile, alkyl or cycloalkyl, each of which is unsubstituted or substituted and/or mono- or polyethylenically unsaturated, or substituted or unsubstituted fullerenyl, aryl, alkoxy, alkoxycarbonyl or alkanoyl, and n is a number from 0 to 6, preferably 0 to 1.

Likewise preferred are those monofunctional aziridine compounds of the formula (I) in which $R^1$ is a radical of the formula

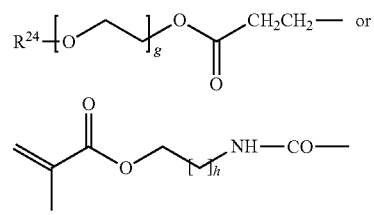

in which $R^{24}$ is —H or alkyl, preferably —H, —$CH_3$, —$C_2H_5$, more preferably —$CH_3$, —$C_2H_5$.

g is a number from 1 to 4, preferably 1 to 3, more preferably 1 to 2, h is a number from 1 to 11, preferably 1 to 5 and more preferably 1 to 3, and the remaining radicals have the above definition.

More particular preference is given to those compounds of the formula (I) which conform to the compound of the formula (III) or (IV),

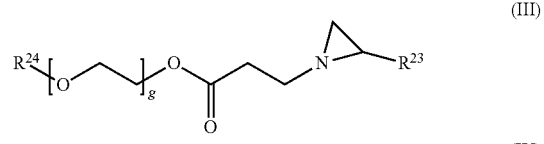
(III)

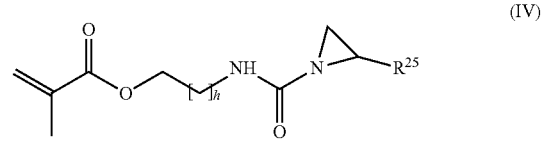
(IV)

where $R^{23}$ is —H or alkyl, preferably —H or —$CH_3$, more preferably —$CH_3$, $R^{25}$ is —H or alkyl, preferably —H or —$CH_3$, more preferably —$CH_3$, and the remaining radicals have the above definition.

Particularly preferred aziridines are those having two or more aziridine functions. Examples include compounds of the formula (V)

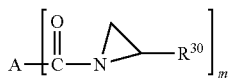

in which

A is an m-valent aliphatic, cycloaliphatic or aromatic radical, which is optionally substituted, m is a number from 2 to 5, more particularly 2 to 3, and $R^{30}$ for each m unit is in each case independently hydrogen or $C_1$-$C_4$ alkyl, more particularly $CH_3$ or $CH_2CH_3$.

Where m is 2, A is preferably $C_2$-$C_{10}$ alkylene, more particularly

—((CH$_2$)$_6$)—, —C(CH$_3$)$_2$CH$_2$C(CH$_3$)$_2$CH$_2$— or

—C(CH$_3$)$_2$CH$_2$CH(CH$_3$)CH$_2$—, or is a phenylene, more particularly the bivalent radical of the formula

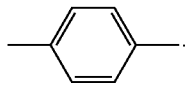

If m is 3, A is preferably the trivalent radical of the formula

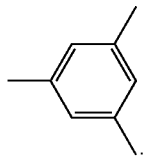

Preferred compounds of the formula (V) are those conforming to the formulae (Va)-(Vd).

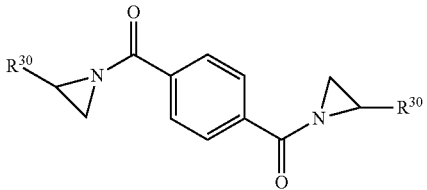

Likewise preferred as polyfunctional aziridine compounds are Michael adducts of optionally substituted ethylenimine with esters of polyhydric alcohols with α,β-unsaturated carboxylic acids and the adducts of optionally substituted ethylenimine with polyisocyanates.

Suitable alcohol components are, for example, trimethylolpropane, neopentylglycol, glycerol, pentaerythritol, 4,4'-isopropylidenediphenol, 4,4'-methylenediphenol and polyvinyl alcohols. Examples of suitable α,β-unsaturated carboxylic acids include acrylic acid and methacrylic acid, crotonic acid and cinnamic acid. Particular preference is given to acrylic acid. The corresponding polyhydric alcohols of the α,β-unsaturated carboxylic esters may optionally be alcohols which have been extended on their OH functions in some cases completely with alkylene oxides, singly or multiply. These may be, for example, the aforementioned alcohols extended singly or multiply with alkylene oxides. In this respect, reference is also made to U.S. Pat. No. 4,605,698, the disclosure content of which is included by reference in the present invention. Alkylene oxides which are particularly suitable in accordance with the invention are ethylene oxide and propylene oxide.

Examples of polyisocyanates suitable for reaction with optionally substituted ethylenimine are those specified at page 4 lines 33-35 of WO 2004/050617.

Examples of aziridines that are suitable in accordance with the invention are those specified at page 3 lines 29-34 of WO 2004/050617.

Preference is likewise given to those aziridines of the kind described, for example, in U.S. Pat. No. 3,225,013 (Fram), U.S. Pat. No. 4,490,505 (Pendergrass) and U.S. Pat. No. 5,534,391 (Wang).

Likewise preferred are those aziridines of the formula (I) which possess at least three aziridine groups, such as, for example, trimethylolpropane tris[3-(1-aziridinyl)propionate], trimethylolpropane tris[3-(2-methyl-1-aziridinyl)propionate], trimethylolpropane tris[2-aziridinylbutyrate], tris(1-aziridinyl)phosphine oxide, tris(2-methyl-1-aziridinyl)phosphine oxide, pentaerythritol tris-[3-(1-aziridinyl)propionate] and pentaerythritol tetrakis-[3-(1-aziridinyl)propionate].

Of these, preference is given particularly to trimethylolpropane tris[3-(1-aziridinyl)propionate], trimethylolpropane tris[3-(2-methyl-1-aziridinyl)propionate], trimethylolpropane tris[2-aziridinylbutyrate], pentaerythritol tris-[3-(1-aziridinyl)propionate] and pentaerythritol tetrakis-[3-(1-aziridinyl)propionate].

Particularly preferred are trimethylolpropane tris[3-(1-aziridinyl)propionate], trimethylolpropane tris[3-(2-methyl-1-aziridinyl)propionate] and pentaerythritol tetrakis-[3-(1-aziridinyl)propionate].

Likewise preferred are polyfunctional aziridines of the formula (VI)

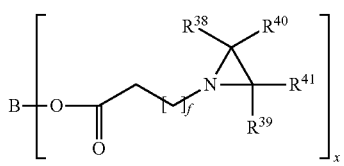

in which
B is the radical of an aliphatic polyol which contains at least x OH functions, where x OH functions are substituted by the radical of the above brackets,
f is a number from 0 to 6, more particularly from 1 to 3,
x is a number greater than or equal to 2, and more particularly is 2 to 500 000, and
$R^{38}$, $R^{39}$, $R^{40}$ and $R^{41}$ have the identical meaning as the radicals $R^2$-$R^5$ in the formula (I).

Particularly preferred aziridines of the formula (VI) are those in which x is 3 or 4 and B is a trebly or quadruply OH-functional polyol.

Particularly preferred aziridines of the formula (VI) are those conforming to the formulae (VIa)-(VIc)

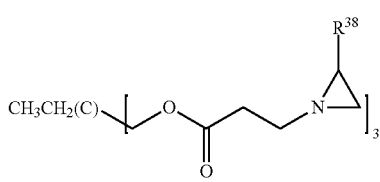

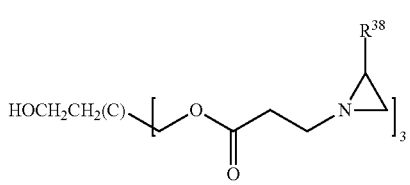

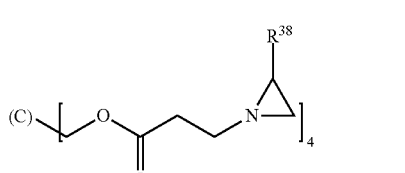

in which
$R^{38}$ is hydrogen or $CH_3$.

A particularly preferred product is the aziridine compound of the formula (VIa), with $R^{38}$=methyl, also known as Crosslinker CX-100 from DSM, and the hardener product "Corial Härter AN" from BASF, which comprises the aziridine of the formula (VIa) with $R^{38}$=hydrogen.

Preferred "alkyl" is a linear or branched alkyl radical having 1 to 20, preferably 1 to 12, carbon atoms. Examples of alkyl radicals according to the invention are methyl, ethyl, n-propyl, isopropyl, n-butyl, isobutyl, sec-butyl, tert-butyl, pentyl, iso-amyl, hexyl, octyl, etc. The aforementioned alkyl radicals may preferably be substituted by the following radicals: alkoxy, preferably $C_1$-$C_{12}$ alkoxy, nitro, monoalkylamino, preferably $C_1$-$C_{12}$ monoalkylamino, dialkylamino, preferably di[$C_1$-$C_{12}$]alkylamino, cyano, halo, haloalkyl, preferably trifluoromethyl, alkanoyl, aminocarbonyl, monoalkylaminocarbonyl, dialkylaminocarbonyl, alkylamido, preferably $C_1$-$C_{12}$ alkylamido, alkoxycarbonyl, preferably $C_1$-$C_{12}$ alkoxycarbonyl, alkylcarbonyloxy, preferably $C_1$-$C_{12}$ alkylcarbonyloxy, aryl, preferably phenyl, or aryl substituted by halogen, $C_1$-$C_{12}$ alkyl or $C_1$-$C_{12}$ alkoxy, or heterocyclic 3-membered-ring groups, more particularly aziridine groups or epoxy groups, or substituents, such as those specified above, which contain these groups.

The nitrogen-containing inorganic carrier materials of the invention may further comprise additional compounds, examples being solvents such as, for example, esters of mono- or polybasic carboxylic acids (e.g. mixtures comprising diisobutyl adipate, diisobutyl glutarate, diisobutyl succinate), preferably VOC-free or low-VOC solvents, where VOC (volatile organic compounds) are compounds having a boiling point of less than 250° C.; and emulsifiers such as, for example, castor oil ethoxylates, dispersing assistants such as, for example, polyvinyl alcohols, chelating reagents such as, for example, those specified in WO 98/22543, one or more stabilizers from the series of the antioxidants, free-radical scavengers, UV stabilizers and/or UV absorbers (for examples see below). In many cases, synergistic effects are observed here. The reaction of the inorganic carrier material may take place for these compounds as well preferably in analogy to method a)-d) (see below).

The nitrogen-containing inorganic carrier materials of the invention are prepared using, for example,
0.001% to 80%, preferably 0.005% to 60%, more particularly 0.01% to 50%, by weight, of at least one nitrogen-containing compound and
20%-99.999%, preferably 40%-99.995%, more preferably 50%-99.99%, by weight, of at least one inorganic carrier material.

As preferred further constituents, the nitrogen-containing inorganic carrier materials of the invention contain 0.0001% to 8%, preferably 0.0005% to 6%, more particularly 0.001% to 5%, by weight, of emulsifiers. The nitrogen-containing inorganic carrier materials of the invention may additionally contain 0.1% to 15%, preferably 0.5% to 10%, more particularly 1% to 6%, by weight, of a solvent.

The invention further relates to a process for producing the nitrogen-containing inorganic carrier materials of the invention, which is characterized in that
a) at least one nitrogen-containing compound, preferably a liquid, nitrogen-containing compound, or solutions of at least one preferably liquid, nitrogen-containing compound in an organic solvent, preferably in a VOC-free or low-VOC solvent, is or are mixed with an inorganic carrier, or
b) at least one nitrogen-containing compound is dissolved in an organic solvent and mixed with an inorganic carrier material, optionally with addition of suitable dispersing assistants, and the nitrogen-containing inorganic carrier material is isolated, or
c) an emulsion comprising at least one nitrogen-containing compound, water, at least one organic solvent and, optionally, emulsifiers is mixed with an inorganic carrier material, and the nitrogen-containing inorganic carrier material is isolated, or
d) an aqueous dispersion of an inorganic carrier material, optionally comprising dispersing assistants, is mixed with an emulsion comprising at least one nitrogen-containing compound, water, at least one organic solvent and optionally emulsifiers, and the nitrogen-containing inorganic carrier material is isolated, or,
e) an aqueous dispersion of an inorganic carrier material, optionally comprising dispersing assistants, is mixed with an aqueous solution comprising at least one nitrogen-containing compound and optionally emulsifiers, and the nitrogen-containing inorganic carrier material is isolated, the isolation of the nitrogen-containing inorganic carrier material obtained according to steps b) to e) taking place preferably by complete or partial removal of the solvent, more particularly by filtration and optional subsequent drying or evaporation of the solvent, as for example by fluidized-bed drying, spray drying or rotary evaporation optionally under reduced pressure.

Process alternative a) relates preferably to heterocyclic 3-membered-ring compounds which are liquid at room temperature (22° C.), with, in particular, pastelike compositions or dry powders being formed.

In the case of process alternative b), preferred dispersants that are suitable are nonionic and anionic emulsifiers.

Particularly preferred are carrier materials obtainable by the process of the invention, more particularly in accordance with procedure b), that comprise a dispersant, preferably anionic emulsifiers such as, for example, alkyl sulphates, alkyl ether sulphates, alkylarylsulphonates, alkyl succinates, alkyl sulphosuccinates, N-alkoylsarcosinates, acyltaurates, acylisethionates, alkyl phosphates, alkyl ether phosphates, alkyl ether carboxylates, alpha-olefinsulphonates, more particularly the alkali metal and alkaline earth metal salts, e.g. sodium, potassium, magnesium, calcium salts and also ammonium salts and triethanolamine salts, or ionic emulsifiers such as, for example, alkylaryl polyglycol ethers, such as polyoxyethylene octylphenol ether, ethoxylated isooctyl-, octyl- or nonylphenol, alkylphenol or tributylphenyl polyglycol ethers, trissteryl phenyl ether ethoxylates, alkylaryl polyether alcohols, isotridecyl alcohol, polyoxyethylene-fatty alcohol ethers, polyoxyethylene-fatty acid esters such as, for example, ethoxylated castor oil, polyoxyethylenealkyl ethers or polyoxypropylene, lauryl alcohol polyglycol ether acetate, sorbitol esters or block copolymers based on ethylene oxide and/or propylene oxide.

In the case of procedure c), preferred organic solvents used for the oil-in-water emulsion are preferably those specified above.

Preference is given to preparation in accordance with process alternative d). In this case, in particular, first of all a dispersion of the inorganic carrier materials in water is prepared with the use preferably of low shearing energy, as for example by using a paddle stirrer.

For all of the procedures, further additions may be made in solid or liquid form or in dissolved, dispersed or emulsified form.

The process alternatives according to the invention take place preferably at a temperature from 0 to 35° C., more particularly at room temperature (22° C.).

The invention further relates to the use of the nitrogen-containing inorganic carrier materials of the invention for stabilizing iodine-containing compounds, more particularly biocides.

Iodine-containing compounds contemplated are preferably iodoalkynyl compounds or compounds in which one or more iodine atoms are attached to double bonds or in which one or more iodine atoms are attached to singly bonded carbon atoms.

The iodine-containing compounds, more particularly biocides, are, for example, diiodomethyl p-tolyl sulphone, diiodomethyl p-chlorophenyl sulphone, 3-bromo-2,3-diiodo-2-propynyl alcohol, 2,3,3-triiodoallyl alcohol, 4-chloro-2-(2-chloro-2-methylpropyl)-5-[(6-iodo-3-pyridinyl)methoxy]-3(2H)-pyridazinone (CAS RN: 120955-77-3), iodofenfos, 3-iodo-2-propynyl 2,4,5-trichlorophenyl ether, 3-iodo-2-propynyl 4-chiorophenyl formal (IPCF), N-iodopropargyloxycarbonylalanine, N-iodopropargyloxycarbonylalanine ethyl ester, 3-(3-iodopropargyl)benzoxazol-2-one, 3-(3-iodiopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate or 3-iodo-2-propynyl cyclohexylcarbamate.

The iodine-containing compounds, more particularly biocides, are preferably 3-iodo-2-propynyl 2,4,5-trichlorophenyl ether, 3-iodo-2-propynyl 4-chiorophenyl formal (IPCF), N-iodopropargyloxycarbonylalanine, N-iodopropargyloxycarbonylalanine ethyl ester. 3-(3-iodopropargyl)benzoxazol-2-one, 3-(3-iodopropargyl)-6-chlorobenzoxazol-2-one, 3-iodo-2-propynyl alcohol, 4-chlorophenyl 3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate or 3-iodo-2-propynyl cyclohexylcarbamate.

With particular preference the iodine-containing compounds, more particularly biocides, are 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate or 3-iodo-2-propynyl cyclohexylcarbamate.

Furthermore, the particularly preferred iodine-containing compounds, more particularly biocides, are N-alkyl-iodotetrazoles, N-aryl-iodotetrazoles and N-aralkyl-iodotetrazoles, as described, for example, in (EP1773125).

The iodine-containing compounds, more particularly biocides, may be used individually or in mixtures together with two or more iodine-containing compounds, more particularly biocides. Particular preference is given to IPBC.

The nitrogen-containing inorganic carrier materials of the invention for use in accordance with the use are suitable preferentially for stabilizing iodine-containing compounds, more particularly biocides, in binder formulations, such as in alkyd-resin-based systems such as coating materials which comprise transition metal dryers, in particular in the presence of transition metal dryers. Preferred binder formulations and transition metal dryers are described in more detail later on below.

Stabilization in the context of this specification means preferably the stabilization of iodine-containing compounds against both chemical and light-induced degradation, particularly against chemical degradation.

The nitrogen-containing inorganic carrier materials of the invention may more particularly be used for suppressing or at least retarding the chemical degradation of iodine-containing compounds, more particularly biocides in active-compound formulations, more particularly coating materials such as paints, varnishes, primers, impregnating systems, stains and other industrial materials. The nitrogen-containing inorganic carrier materials of the invention that can be used in accordance with the invention for stabilizing iodine-containing compounds, more particularly biocides, have a good stabilizing action especially in alkyd-resin-based systems such as coating materials which comprise transition metal dryers.

The stabilization is preferably realized by the iodine-containing compounds, more particularly biocides, and the nitrogen-containing inorganic carrier materials of the invention being present together in a mixture or in a medium.

Preference is given to employing a composition comprising
a) at least one nitrogen-containing inorganic carrier material of the invention
and
b) at least one iodine-containing biocide.

The composition is likewise provided by the present invention.

With regard to the preferred iodine-containing compounds, more particularly biocides, and the preferred carrier materials of the invention, the forms of preference specified above apply to the preferred compositions of the invention as well.

Particularly preferred compositions comprise
a) at least one nitrogen-containing inorganic carrier material, and
b) IPBC.

The compositions of the invention contain generally 0.01-70%, preferably 0.05%-60%, more preferably 0.1%-50% by weight of at least one iodine-containing biocide and at least one nitrogen-containing inorganic carrier material of the invention, and so the amount of all of the nitrogen-containing inorganic carrier materials present in the composition of the invention is 0.001%-80%, preferably 0.005%-60%, more preferably 0.01-50% by weight.

The composition of the invention preferably comprises the iodine-containing biocide and nitrogen-containing inorganic carrier materials in total from 40% to 99% by weight.

In the context of the inventive use, the nitrogen-containing inorganic carrier material of the invention is preferably employed, and the amount of all of the nitrogen-containing inorganic carrier materials present in the composition of the invention is generally 1% to 280%, more preferably 2% to 225%, more particularly 5% to 180%, by weight, based on the iodine-containing biocide.

The composition of the invention may be present in a variety of forms—for example, as a solvent-based dispersion, water-based dispersion, solids mixture, etc.

With particular preference, the composition of the invention takes the form of a solid mixture, such as, for example, a powder or granules, more particularly having an average particle size of 50 to 2000 µm, or a compacted formulation, such as, for example, compacted powder such as, for example, pellets, tablets, etc.

Likewise with particular preference, the composition of the invention takes the form of a solvent-based dispersion, where, in order to adjust the rheological properties of the dispersion, for example, alkyd resins, modified alkyd resins, thixotropic resins, etc., and also further additives such as anti-skinning agents (antioxidants), pigments, crystallization stabilizers, etc., may be added.

Further possible ingredients of the composition of the invention that may be included are adhesives such as carboxymethylcellulose, natural and synthetic polymers in powder, particle or latex form, such as gum arabic, polyvinyl alcohol, polyvinyl acetate, and also natural phospholipids, such as cephalins and lecithins, and synthetic phospholipids, and also mineral and vegetable oils. Moreover, it may comprise colorants such as inorganic pigments, e.g. iron oxide, titanium oxide, Prussian Blue, and organic dyes, such as alizarin dyes, azo dyes and metal phthalocyanine dyes, and trace nutrients, such as salts of iron, manganese, boron, copper, cobalt, molybdenum and zinc, and also stabilizers known for heterocyclic 3-membered-ring compounds, in particular aziridine compounds, examples being tetramethylethylenediamine (TMEDA), triethylenediamine, and the 1,4-diazabicyclo[2.2.2]octane (DABCO) known from WO 2004/050617.

The invention further provides a process for preparing the composition of the invention.

The composition of the invention may be prepared, for example, by mixing the individual components, i.e. the nitrogen-containing inorganic carrier material and the iodine-containing compound, optionally with extenders and optionally using further adjuvants such as, for example, flow improvers, additives for increasing the electrical conductivity, additives for adjusting the dusting characteristics, etc. For preparing the composition of the invention in the form of solids mixtures, use is made here, optionally after pretreatment of the components that are to be mixed, using, for example, sieve mills such as the Bauermeister mill, of suitable solids mixers such as, for example, Lödige mixers, paddle mixers, tumble mixers, drum mixers with disruptors, etc. Additionally, the conversion of resultant solids mixtures into further embodiments, such as granules, compacted forms such as pillows, tablets, etc., for example is possible with use of fluid-bed granulation, use of mechanical compacting systems, optionally with addition of further additives such as binders, for example.

Another embodiment of the composition of the invention is a solvent-based dispersion comprising an iodine-containing compound, in particular IPBC, and at least one nitrogen-containing inorganic carrier material of the invention, in particular one in which the heterocyclic 3-ring compound is at least one aziridine compound. In this case, the iodine-containing compound, in particular IPBC, and the nitrogen-containing inorganic carrier material of the invention are ground and dispersed (e.g. bead mill), preferably with strong shearing in an inert organic solvents as the continuous phase (e.g. isoparaffins such as Isopar® L (isoparaffin from Exxon) or "white spirits" such as, for example, Shellsol® D60), optionally with addition of process auxiliaries and stabilizers such as, for example, rheological additives (thixotroping resins such as, for example, WorleeThix S6358, a thixotroped alkyd resin from Worlee) and optionally anti-skinning agents such as, for example, Antiskin® 444 (from Borchers).

The activity and the spectrum of action of the compositions of the invention and/or of the iodine-containing compound employed may be increased by adding, optionally, further antimicrobial compounds, fungicides, bactericides, herbicides, insecticides or other active compounds, so as to widen the spectrum of activity or to obtain particular effects, or by using such compounds at the same time. These mixtures may possess an even broader spectrum of action.

In many cases, synergistic effects are obtained, i.e. the activity of the mixture is greater than the activity of the individual components. The following compounds, for example, are particularly favourable co-components:
triazoles such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, myclobutanil, metconazole, paclobutrazole, penconazole, propioconazole, prothioconazole, simeconazole, (±)-cis-1-(4-chlorophenyl)-2-(1H-1,2,4-triazol-1-yl)cycloheptanol, 2-(1-tert-butyl)-1-(2-chlorophenyl)-3-(1,2,4-triazol-1-yl) propan-2-ol, tebuconazole, tetraconazole, triadimefon, triadimenol, triapenthenol, triflumizole, triticonazole, uniconazole and their metal salts and acid adducts;

imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;

pyridines and pyrimidines such as:
ancymidol, buthiobate, fenarimol, mepanipyrin, nuarimol, pyvoxyfur, triamirol;

succinate dehydrogenase inhibitors such as:
benodanil, carboxim, carboxim sulphoxide, cyclafluramid, fenfuram, flutanil, furcarbanil, furmecyclox, mebenil, mepronil, methfuroxam, metsulphovax, nicobifen, pyracarbolid, oxycarboxin, Shirlan, Seedvax;

naphthalene derivatives such as:
terbinafine, naftifine, butenafine, 3-chloro-7-(2-aza-2,7,7-trimethyloct-3-en-5-yne);

sulphenamides such as:
dichlofluanid, tolylfluanid, folpet, fluorofolpet, captan, captofol;

benzimidazoles such as:
carbendazim, benomyl, fuberidazole, thiabendazole or their salts;

morpholine derivatives such as:
aldimorph, dimethomorph, dodemorph, falimorph, fenpropidin, fenpropimorph, tridemorph, trimorphamid and their arylsulphonate salts such as, for example, p-toluenesulphonic acid and p-dodecylphenylsulphonic acid;

benzothiazoles such as:
2-mercaptobenzothiazole;

benzothiophene dioxides such as:
N-cyclohexyl-benzo[b]thiophenecarboxamide S,S-dioxide;

benzamides such as:
2,6-dichloro-N-(4-trifluoromethylbenzyl)benzamide, tecloftalam;

boron compounds such as:
boric acid, boric esters, borax;

formaldehyde and formaldehyde-releasing compounds such as:
benzyl alcohol mono(poly)hemiformal, 1,3-bis(hydroxymethyl)-5,5-dimethylimidazolidine-2,4-dione (DMDMH), bisoxazolidine, n-butanol hemiformal, cis-1-(3-chloroallyl)-3,5,7-triaza-1-azoniaadamantane chloride, 1-[1,3-bis(hydroxymethyl-2,5-dioxoimidazolidin-4-yl]-1,3-bis(hydroxymethyl)urea, dazomet, dimethylolurea, 4,4-dimethyloxazolidine, ethylene glycol hemiformal, 7-ethylbicyclooxazolidine, hexahydro-S-triazine, hexamethylenetetramine, N-hydroxymethyl-N'-methylthiourea, methylenebismorpholine, sodium N-(hydroxymethyl)glycinate, N-methylolchloroacetamide, oxazolidine, paraformaldehyde, taurolin, tetrahydro-1,3-oxazine, N-(2-hydroxypropyl) aminemethanol, tetramethylolacetylenediurea (TMAD);

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octylisothiazolin-3-one, 4,5-trimethyleneisothiazolinone, 4,5-benzoisothiazolinone;

aldehydes such as:
cinnamaldehyde, formaldehyde, glutaraldehyde, β-bromocinnamaldehyde, o-phthalaldehyde;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzyldimethyldodecylammonium chloride, dichlorobenzyldimethylalkylammonium chloride, didecyldimethylammonium chloride, dioctyldimethylammonium chloride, N-hexadecyltrimethylammonium chloride, 1-hexadecylpyridinium chloride, iminoctadine tris(albesilate);

phenols such as:
tribromophenol, tetrachlorophenol, 3-methyl-4-chlorophenol, 3,5-dimethyl-4-chlorophenol, dichlorophene, 2-benzyl-4-chlorophenol, triclosan, diclosan, hexachlorophene, methyl p-hydroxybenzoate, ethyl p-hydroxybenzoate, propyl p-hydroxybenzoate, butyl p-hydroxybenzoate, octyl p-hydroxybenzoate, o-phenylphenol, m-phenylphenol, p-phenylphenol, 4-(2-tert-butyl-4-methylphenoxy)phenol, 4-(2-isopropyl-4-methylphenoxy)phenol, 4-(2,4-dimethylphenoxy)phenol and their alkali metal salts and alkaline earth metal salts;

microbicides with an activated halogen group such as:
bronopol, bronidox, 2-bromo-2-nitro-1,3-propanediol, 2-bromo-4'-hydroxyacetophenone, 1-bromo-3-chloro-4,4,5,5-tetramethyl-2-imidazolidinone, β-bromo-β-nitrostyrene, chloracetamide, chloramine T, 1,3-dibromo-4,4,5,5-tetramethyl-2-imidazolidinone, dichloramine T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl 2-chlorocyanovinyl sulphone, phenyl 1,2-dichloro-2-cyanovinyl sulphone, trichloroisocyanuric acid;

pyridines such as:
1-hydroxy-2-pyridinethione (and the Cu, Na, Fe, Mn, Zn salts thereof), tetrachloro-4-methyl-sulphonylpyridine, pyrimethanol, mepanipyrim, dipyrithion, 1-hydroxy-4-methyl-6-(2,4,4-trimethylpentyl)-2(1H)-pyridine;

methoxyacrylates or similar such as:
azoxystrobin, dimoxystrobin, fluoxastrobin, kresoxim-methyl, metominostrobin, orysastrobin, picoxystrobin, pyraclostrobin, trifloxystrobin, 2,4-dihydro-5-methoxy-2-methyl-4-[2-[[[[1-[3-(trifluoromethyl)phenyl]ethylidene] amino]oxy]methyl]phenyl]-3H-1,2,4-triazol-3-one (CAS No. 185336-79-2);

metal soaps such as:
salts of the metals tin, copper and zinc with higher fatty acids, resin acids, naphthenic acids and phosphoric acid, such as, for example, tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate, zinc benzoate;

metal salts such as:
salts of the metals tin, copper, zinc, and also chromates and dichromates, such as, for example, copper hydroxycarbonate, sodium dichromate, potassium dichromate, potassium chromate, copper sulphate, copper chloride, copper borate, zinc fluorosilicate, copper fluorosilicate;

oxides such as:
oxides of the metals tin, copper and zinc, such as, for example, tributyltin oxide, $Cu_2O$, $CuO$, $ZnO$;

oxidizing agents such as:
hydrogen peroxide, peracetic acid, potassium persulphate;
dithiocarbamates such as:
cufraneb, ferban, potassium N-hydroxymethyl-N'-methyldithiocarbamate, sodium dimethyldithiocarbamate, potassium dimethyldithiocarbamate, mancozeb, maneb, metam, metiram, thiram, zineb, ziram;
nitriles such as:
2,4,5,6-tetrachloroisophthalonitrile, disodium cyanodithioimidocarbamate;
quinolines such as:
8-hydroxyquinoline and the copper salts thereof;
other fungicides and bactericides such as:
bethoxazin, 5-hydroxy-2(5H)-furanone, 4,5-benzodithiazolinone, 4,5-trimethylenedithiazolinone, N-(2-p-chlorobenzoylethyl)hexaminium chloride, 2-oxo-2-(4-hydroxyphenyl)acetohydroxy-cinnamoyl chloride, tris-N-(cyclohexyldiazeniumdioxy)-aluminium, N-(cyclohexyldiazenium-dioxy)-tributyltin or its potassium salts, bis-N-(cyclohexyldiazeniumdioxy) copper, iprovalicarb, fenhexamide, spiroxamine, carpropamid, diflumetorin, quinoxyfen, famoxadone, polyoxorim, acibenzolar S-methyl, furametpyr, thifluzamide, methalaxyl-M, benthiavalicarb, metrafenon, cyflufenamid, tiadinil, tea tree oil, phenoxyethanol,
Ag, Zn or Cu-containing zeolites alone or incorporated into polymeric materials.

Very especially preferred are mixtures with
azaconazole, bromuconazole, cyproconazole, dichlobutrazol, diniconazole, diuron, hexaconazole, metaconazole, penconazole, propiconazole, tebuconazole, dichlofluanid, tolylfluanid, fluorfolpet, methfuroxam, carboxin, N-cyclohexyl-benzo[b]thiophenecarboxamnide S,S-dioxide, fenpiclonil, 4-(2,2-difluoro-1,3-benzodioxol-4-yl)-1H-pyrrole-3-carbonitrile, butenafine, imazalil, N-methylisothiazolin-3-one, 5-chloro-N-methylisothiazolin-3-one, N-octylisothiazolin-3-one, dichloro-N-octylisothiazolinone, mercaptobenzothiazole, thiocyanatomethylthiobenzothiazole, thiabendazole, benzoisothiazolinone, N-(2-hydroxypropyl)aminomethanol, benzyl alcohol (hemi)formal, N-methylolchloroacetamide, N-(2-hydroxypropyl)aminemethanol, glutaraldehyde, ornadine, Zn-ornadine, dimethyl dicarbonate, 2-bromo-2-nitro-1,3-propanediol, bethoxazin, o-phthalialdehyde, 2,2-dibromo-3-nitrilepropionamide, 1,2-dibromo-2,4-dicyanobutane, 1,3-bis(hydroxymethyl)-5,5-dimethylimidazolidine-2,4-dione (DMDMH), tetramethylolacetylenediurea (TMAD), ethylene glycol hemiformal, p-hydroxybenzoic acid, carbendazim, chlorophen, 3-methyl-4-chlorophenol, o-phenylphenol.

Apart from with the abovementioned fungicides and bactericides, mixtures with a good efficacy are, moreover, also prepared with other active compounds:
insecticides/acaricides/nematicides:
abamectin, acephate, acetamiprid, acetoprole, acrinathrin, alanycarb, aldicarb, aldoxycarb, aldrin, allethrin, alpha-cypermethrin, amidoflumet, amitraz, avermectin, azadirachtin, azinphos A, azinphos M, azocyclotin,
*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bistrilfluron, bromophos A, bromophos M, bufencarb, buprofezin, butathiophos, butocarboxim, butoxycarboxim,
cadusafos, carbaryl, carbofuran, carbophenotion, carbosulphan, cartap, quinomethionate, cloethocarb, chlordane, chlorethoxyfos, chlorfenapyr, chlorfenvinphos, chlorfluazuron, chlormephos, N-[(6-chloro-3-pyridinyl)methyl]-N'-cyano-N-methylethaneinidamide, chlorpicrin, chlorpyrifos A, chlorpyrifos M, cis-resmethrin, clocythrin, clothiazoben, cypophenothrin, clofentezin, coumaphos, cyanophos, cycloprothrin, cyfluthrin, cyhalothrin, cyhexatin, cypermethrin, cyromazin,
decamethrin, deltamethrin, demeton M, demeton S, demeton-S-methyl, diafenthiuron, dialiphos, diazinon, 1,2-dibenzoyl-1(1,1-dimethyl)hydrazine, DNOC, dichlofenthion, dichlorvos, dicliphos, dicrotophos, difethialone, diflubenzuron, dimethoate, 3,5-dimethylphenyl methylcarbamate, dimethyl(phenyl)silylmethyl-3-phenoxybenzyl ether, dimethyl(4-ethoxyphenyl)silylmethyl-3-phenoxybenzyl ether, dimethylvinphos, dioxathion, disulphoton,
eflusilanate, emamectin, empenthrin, endosulphan, EPN, esfenvalerate, ethiofencarb, ethion, ethofenprox, etrimphos, etoxazole, etobenzanid,
fenamiphos, fenazaquin, fenbutatin oxide, fenfluthrin, fenitrothion, fenobucarb, fenothiocarb, fenoxycarb, fenpropathrin, fenpyrad, fenpyroximate, fensulphothion, fenthion, fenvalerate, fipronil, flonicamid, fluacrypyrim, fluazuron, flucycloxuron, flucythrinate, flufenerim, flufenoxuron, flupyrazofos, flufenzine, flumethrin, flufenprox, fluvalinate, fonophos, formethanate, formothion, fosmethilan, fosthiazate, fubfenprox, furathiocarb,
halofenozide, HCH, (CAS RN: 58-89-9), heptenophos, hexaflumuron, hexythiazox, hydramethylnon, hydroprene, imidacloprid, imiprothrin, indoxycarb, iprinomectin, iprobenfos, isazophos, isoamidophos, isofenphos, isoprocarb, isoprothiolane, isoxathion, ivermectin,
kadedrin,
lambda-cyhalothrin, lufenuron,
malathion, mecarbam, mervinphos, mesulphenphos, metaldehyde, methacrifos, methamidophos, methidathion, methiocarb, methomyl, metolcarb, milbemectin, monocrotophos, moxiectin,
naled, NI 125, nicotine, nitenpyram, noviflumuron,
omethoate, oxamyl, oxydemethon M, oxydeprofos,
parathion A, parathion M, penfluron, permethrin, 2-(4-phenoxyphenoxyl)ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyridalyl, pyrimidifen, pyriproxifen, pyrithiobac-sodium,
quinalphos,
resmethrin, rotenone,
salithion, sebufos, silafluofen, spinosad, spirodiclofen, spiromesifen, sulphotep, sulprofos,
tau-fluvalinate, taroils, tebufenozide, tebufenpyrad, tebupirimphos, teflubenzuron, tefluthrin, temephos, terbarn, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron, trichlorfon, triflumuron, trimethacarb,
vamidothion, xylylcarb, zetamethrin;
molluscicides:
fentin acetate, metaldehyde, methiocarb, niclosamide;
herbicides and algicides:
acetochlor, acifluorfen, aclonifen, acrolein, alachlor, alloxydim, ametryn, amidosulphuron, amitrole, ammonium sulphamate, anilofos, asulam, atrazine, azafenidin, aziptrotryne, azimsulphuron,
benazolin, benfluralin, benfuresate, bensulphuron, bensulphide, bentazone, benzofencap, benzthiazuron, bifenox, bispyribac, bispyribac-sodium, borax, bromacil, bromobutide, bromofenoxim, bromoxynil, butachlor, butamifos, butrulin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulphuron, chlorthal, chlorthiamid, cinmethylin, cinosulphuron, clefoxydim, clethodim, clomazone, chlomeprop, clopyralid, cyanamide, cyanazine, cycloate, cycloxydim, chloroxynil, clodinafop-propargyl, cumyluron, clometoxyfen, cyhalofop, cyhalofop-butyl, clopyrasuluron, cyclosulphamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ethametsulphuron, ethoxysulphuron, fenoxaprop, fenoxaprop-P, fenuron, flamprop, flamprop-M, flazasulphuron, fluazifop, fluazifop-P, fuenachlor, fluchloralin, flufenacet, flumeturon, fluorocglycofen, fluoronitrofen, flupropanate, flurenol, fluridone, flurochloridone, fluroxypyr, fomesafen, fosamine, fosametine, flamprop-isopropyl, flamprop-isopropyl-L, flufenpyr, flumiclorac-pentyl, flumipropyn, flumioxzim, flurtamone, flumioxzim, flupyrsulphuron-methyl, fluthiacet-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulphuron, imazomox, isoxaflutole, imazapic, ketospiradox, lactofen, lenacil, linuron, MCPA, MCPA-hydrazide, MCPA-thioethyl, MCPB, mecoprop, mecoprop-P, mefenacet, mefluidide, mesosulphuron, metam, metamifop, metamitron, metazachlor, methabenzthiazuron, methazole, methoroptryne, methyldymron, methyl isothiocyanate, metobromuron, metoxuron, metribuzin, metsulphuron, molinate, manolide, monolinuron, MSMA, metolachlor, metosulam, metobenzuron, naproanilide, napropamide, naptalam, neburon, nicosulphuron, norflurazon, sodium chlorate, oxadiazon, oxyfluorfen, oxysulphuron, orbencarb, oryzalin, oxadiargyl, propyzamide, prosulphocarb, pyrazolate, pyrazosulphuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulphuron, prodiamine, profoxydim, prometryn, propachlor, propanil, propaquizafob, propazine, propham, propisochlor, pyriminobac-methyl, pelargonic acid, pyrithiobac, pyraflufen-ethyl, quinmerac, quinocloamine, quizalofop, quizalofop-P, quinchlorac, rimsulphuron, sethoxydim, sifuron, simazine, simetryn, sulphosulphuron, sulphometuron, sulphentrazone, sulcotrione, sulphosate, tar oils, TCA, TCA-sodium, tebutam, tebuthiuron, terbacil, terbumeton, terbuthylazine, terbutryn, thiazafluoron, thifensulphuron, thiobencarb, thiocarbazil, tralkoxydim, triallate, triasulphuron, tribenuron, triclopyr, tridiphane, trietazine, trifluoralin, tycor, thdiazimin, thiazopyr, triflusulphuron, vernolate, The invention further provides a binder formulation comprising
  at least one binder,
  at least one iodine-containing compound, more particularly biocide, and
  at least one nitrogen-containing inorganic carrier material of the invention.

The binder formulation preferably comprises the 'iodine-containing compound, more particularly biocide', and 'nitrogen-containing inorganic carrier materials of the invention' components in the form of the composition of the invention. Preferred binders contemplated include oxidatively drying binders, preferably alkyd-resin-based binders, or binders which form films by means of coalescents, especially latices.

The alkyd-resin-based binders contemplated are preferably alkyd resins and modified alkyd resins.

The alkyd resins are, in general, polycondensation resins formed from polyols and polybasic carboxylic acids and/or their anhydrides, and fats, oils or free natural and/or synthetic fatty acids. The alkyd resins may optionally also be modified chemically with hydrophilic groups, especially water-soluble groups, in order that they can be used, for example, as an emulsifiable or as a water-soluble alkyd resin.

The stated polyols are preferably glycerol, pentaerythritol, trimethylolethane, trimethylolpropane and various diols such as ethane-/propanediol, diethylene glycol and neopentyl glycol.

The stated polybasic carboxylic acids and/or their anhydrides are preferably phthalic acid, phthalic anhydride, maleic anhydride, isophthalic acid, terephthalic acid, trimellitic anhydride, adipic acid, azelaic acid or sebacic acid.

The stated oils or fatty acids are generally linseed oil, oiticica oil, tung oil, soya oil, sunflower oil, safflower oil, ricinene oil, tall oil, castor oil, coconut oil, peanut oil, their fatty acids, and also synthetic saturated, unsaturated or polyunsaturated monocarboxylic acids or mixtures of these components.

The alkyd resins can optionally also be modified with, for example, natural resins, phenolic resins, acrylic resins, styrene, epoxy resins, silicone resins, isocyanates, polyamides or aluminium alkoxides.

The alkyd resins generally have a molar mass of 500 to 100 000 g/mol, preferably of 1000 to 50 000 g/mol, more particularly of 1500 to 20 000 g/mol, (determined by laser light scattering; see, for example, "Static Light Scattering of Polystyrene Reference Materials: Round Robin Test", U. Just, B. Werthmann International Journal of Polymer Analysis and Characterization, 1999 Vol. 5, pages 195-207).

The binder formulations of the invention comprise preferably 1% to 80%, more preferably 2% to 70% and with particular preference 3% to 60% by weight of alkyd resin.

The binder formulation of the invention preferably comprises an alkyd-resin-based binder and a transition metal dryer for oxidative drying. Transition metal dryers for the purposes of this specification are more particularly transition metal compounds which accelerate the drying and curing of the alkyd-resin-based binder.

Preference is given to the salts of transition metals of groups Vb, VIb, VIb, VIII and Ib of the chemical periodic system. These are more particularly the salts of cobalt, manganese, vanadium, nickel, copper and iron, more preferably cobalt, manganese, iron and vanadium. They need not necessarily be used alone, but instead can also be employed in combination with non-transition metal salts, such as lead, calcium or zirconium, for example.

The preferred transition metal salts are soluble in organic solvents, for example, white spirit at 20° C. in an amount of more than 10 g/l. The salts in question are preferably the salts of carboxylic acids, which have high compatibility with the alkyd resin binders and at the same time ensure sufficient solubility of the metal salt. Preference is given to using transition metal salts of fatty acids, such as oleates or linoleates, resin acids such as resinates, or salts of 2-ethylhexanoic acid (octoates). Preferred transition metal dryers are cobalt octoate and cobalt naphthenate, e.g. Octasoligen®-Cobalt 12 from Borchers.

The binder formulations of the invention preferably comprise the transition metal dryers in an amount of 0.001% to 1%, preferably 0.005% to 0.5% and very preferably 0.01% to 0.1% by weight, based in each case on binder.

In one preferred embodiment the binder formulations comprise at least one polar organic solvent, preferably a polar aprotic solvent. Examples of suitable such polar protic solvents are those such as dipropylene glycol monomethyl ether (e.g. Dowanol DPM from Dow Chemical) and also, preferably, in combination thereto, polar aprotic solvents, such as dimethylformamide and dimethyl sulphoxide, and also, for example, etherified glycols, oligoglycols and polyglycols, etherified polyols and esterified polyols, esters of monobasic and polybasic carboxylic acids, e.g. diisobutyl adipate, diisobutyl maleate, (e.g. Rhodiasolv DIB).

Particular preference is given to the binder formulation comprising
1% to 80%, preferably 2% to 70%, more preferably 3% to 60% by weight of alkyd resin binder(s)
0% to 50%, preferably 0% to 45%, more preferably 0% to 40% by weight of colour pigments
0.01% to 5%, preferably 0.05% to 3%, more preferably 0.1% to 2% by weight of iodine-containing compound, in particular biocide,
0.001% to 7%, preferably 0.005% to 5%, more preferably 0.01 to 4% by weight of nitrogen-containing inorganic carrier materials,
2% to 97% by weight of solvent(s), more particularly non-polar or polar solvents, including preferably up to 10%, more particularly 0.01% to 7.5%, by weight, based on the binder preparation, of polar aprotic solvents, and
0.001% to 3% by weight of a transition metal dryer.

Particularly preferred binder formulations of the invention are those comprising at least one alkyd resin, at least one transition metal dryer, IPBC, at least one solvent and at least one nitrogen-containing inorganic carrier material of the invention.

The binder formulation may further comprise fillers, anti-skinning agents, rheological additives such as, for example, anti-settling agents and thixotropic agents, further biocides such as fungicides, bactericides, anti-fouling agents and algicides, solvents, process additives, plasticizers, UV stabilizers and heat stabilizers, and also corrosion inhibitors, in customary amounts.

It is additionally possible to add further stabilizers to the binder formulations, examples being the chelating reagents specified in WO 98/22543, or heterocyclic 3-membered-ring compounds, in particular those with a different heteroatom from nitrogen, such as for example the organic epoxides specified in WO 00/16628. In many cases synergistic effects are observed here.

In the context of the inventive use it is also possible, furthermore, to add one or more stabilizers from the group consisting of antioxidants, free-radical scavengers, UV stabilizers, chelators and UV absorbers, which in some cases exhibit synergistic effects.

Further UV stabilizers that may be mentioned include, by way of example, the following:
sterically hindered phenols, such as
2,6-di-tert-butyl-4-methylphenol, 2-tert-butyl-4,6-dimethylphenol, 2,6-dicyclopentyl-4-methylphenol, 2-(α-methylcyclohexyl)-4,6-dimethylphenol, 2,6-di-octadecyl-4-methylphenol or 2,6-di-tert-butyl-4-methoxymethylphenol, diethyl(3,5-di-tertbutyl-4-hydroxybenzyl)phosphonate, 2,4-dimethyl-6-(1-methylpentadecyl)phenol, 2-methyl-4,6-bis[(octylthio)methyl]phenol, 2,6-di-tert-butyl-4-methoxyphenol, 2,5-di-tert-butylhydroquinone, 2,5-di-ter-amylhydroquinone, 2,6-diphenyl-4-octadecyloxyphenol, 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 2,2'-methylenebis(6-tert-butyl-4-methylphenol), 2,2'-methylenebis(4-methyl-6-cyclohexylphenol), 2,2'-methylenebis(4,6-di-tert-butylphenol), 2,2'-ethylidenebis(4,6-di-tert-butylphenol), 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 1,1,3-tris(5-tert-butyl-4-hydroxy-2-methylphenyl)butane, 1,3,5-tri(3,5-di-tert-butyl-4-hydroxybenzyl)-2,4,6-trimethylbenzene, isooctyl 3,5-di-tert-butyl-4-hydroxybenzylmercaptoacetate, 1,3,5-tris(3,5-di-tert-butyl-4-hydroxybenzyl) isocyanurate, 1,3,5-tris(4-tert-butyl-3-hydroxy-2,6-dimethylbenzyl)isocyanurate, 1,3,5-tris[(3,5-di-tert-butyl-4-hydroxyphenyl) propionyloxyethyl]isocyanurate, dioctadecyl 3,5-di-tert-butyl-4-hydroxybenzylphosphonate, calcium monoethyl 3,5-di-tert-butyl-4-hydroxybenzylphosphonate, N,N'-di-(3,5-di-tert-butyl-4-hydroxyphenylpropionyl) hexamethylenediamine, N,N'-di-(3,5-di-tert-butyl-4-hydroxyphenylpropionyl)trimethylenediamine, N,N'-di-(3, 5-di-tert-butyl-4-hydroxyphenylpropionyl)hydrazine, 3,9-bis[1,1-dimethyl-2-[(3-tert-butyl-4-hydroxy-5-methylphenyl)-propionyloxy]ethyl]-2,4,8,10-tetraoxaspiro [5.5]undecane, bis[3,3-bis(4'-hydroxy-3'-tert-butyl-phenyl) butanoic acid]ethylene glycol ester, 2,6-bis[[3-(1,1-dimethylethyl)-2-hydroxy-5-methylphenyl]octahydro-4,7-methano-1H-indenyl]-4-methylphenol (=Wingstay L), 2,4-bis(n-octylthio)-6-(3,5-di-tert-butyl-4-hydroxyphenylamino)-s-triazine N-(4-hydroxyphenyl)-octadecaneamide, 2,4-di-tert-butylphenyl 3',5'-di-tert-butyl-4'-hydroxybenzoate, (benzoic acid, 3,5-bis(1,1-dimethylethyl)-4-hydroxy-, hexadecyl ester), 3-hydroxyphenyl benzoate, 2,2'-methylenebis(6-tert-butyl-4-methylphenol)monoacrylate, 2-(1,1-dimethylethyl)-6-[1-[3-(1,1-dimethylethyl)-5-(1,1-dimethylpropyl)-2-hydroxyphenyl]ethyl]-4-(1,1-dimethylpropyl)phenyl ester, esters of β-(3,5-di-tert-butyl-4-hydroxyphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide, esters of β-(5-tert-butyl-4-hydroxy-3-methylphenyl)propionic acid with monohydric or polyhydric alcohols such as, for example, with methanol, octadecanol, 1,6-hexanediol, neopentyl glycol, thiodiethylene glycol, diethylene glycol, triethylene glycol, pentaerythritol, trishydroxyethyl isocyanurate or dihydroxyethyloxalamide.

Hindered amines, such as
bis(1,2,2,6,6-pentamethyl-4-piperidyl) 2-(3,5-di-tert-butyl-4-hydroxybenzyl)-2-butylmalonate, bis(2,2,6,6-tetramethyl-4-piperidyl)decanedioate, dimethyl succinate-1-(2-hydroxyethyl)-4-hydroxy-2,2,6,6-tetramethylpiperidine copolymer, poly[[6-[(1,1,3,3-tetramethylbutyl)amino]-1,3,5-triazine-2,4-diyl][(2,2,6,6-tetramethyl-4-piperidyl)imino]hexamethylene[(2,2,6,6-tetramethyl-4-piperidyl)imino]] (CAS No. 71878-19-8), 1,5,8,12-tetrakis[4,6-bis(n-butyl-n-1,2,2,6,6-pentamethyl-4-piperidylamino)-1,3,5-triazin-2-yl]-1,5,8,12-tetraazadodecane (CAS No. 106990-43-6), bis(1,2,2,6,6-pentamethyl-4-piperidyl)decanedioate, bis(1,2,2,6,6-pentamethyl-4-piperidyl) 2-(3,5-di-tert-butyl-4-hydroxybenzyl)-2-butylmalonate, decanedioic acid, bis(2,2,6,6-tetramethyl-4-piperidinyl) ester, reaction products with tert-butyl hydroperoxide and octane (CAS No. 129757-67-1), Chimasorb 2020 (CAS No. 192268-64-7), poly[[6-morpholino-1,3,5-triazine-2,4-diyl]][(2,2,6,6-tetramethyl-4-piperidinyl)imino]-1,6-hexanediyl[(2,2,6,6-tetramethyl-4-piperidinyl)imino]], poly[[6-(4-morpholinyl)-1,3,5-triazine-2,4-diyl]][(1,2,2,6,6-pentamethyl-4-piperidinyl)imino]-1,6-hexanediyl[(1,2,2,6,6-pentamethyl-4-piperidinyl)imino]] (9CI), 3-dodecyl-1-(2,2,6,6-tetramethyl-4-piperidyl)pyrrolidine-2,5-dione, 3-dodecyl-1-(1,2,2,6,6-pentamethylpiperidin-4-yl)pyrrolidine-2,5-dione, 4-octadecanoyloxy-2,2,6,6-tetramethylpiperdine, poly[[6-(cyclohexylamino)-1,3,5-triazine-2,4-diyl][(2,2,6,6-tetramethyl-4-piperidinyl)imidno]-1,6-hexanediyl[(2,2,6,6-tetramethyl-4-piperidinyl)imino]], 1H,4H,5H,8H-2,3a,4a,6,7a,8a-hexaazacyclopenta[def]fluorene-4,8-dione, hexahydro-2,6-bis(2,2,6,6-tetramethyl-4-piperidinyl)-(CAS No. 109423-00-9), N,N'-bis(formyl)-N,N'-bis(2,2,6,6-tetramethyl-4-piperidyl)-1,6-hexanediamine, N-(tetramethyl-4-piperidinyl)maleimide-C20-24-α-olefin copolymer (CAS No. 199237-39-3), tetrakis(1,2,2,6,6-pentamethyl-4-piperidyl) 1,2,3,4-butanetetracarboxylate, tetrakis(2,2,6,6-tetramethyl-4-piperidyl) 1,2,3,4-butanetetracarboxylate, 1,2,2,6,6-pentamethyl-4-piperidinyl tridecyl 1,2,3,4-butanetetracarboxylate, (1,2,3,4-butanetetracarboxylic acid, 2,2,6,6-tetramethyl-4-piperidinyl tridecyl ester), (2,4,8,10-tetraoxaspiro[5.5]undecane-3,9-diethanol, β,β,β',β'-tetramethyl-, polymer with 1,2,3,4-butanetetracarboxylic acid) (CAS No. 115055-30-6), 2,4,4-tetramethyl-21-oxo-7-oxa-3,20-diazadispiro[5.1.11.2]heneicosane, (7-oxa-3,20-diazadispiro[5.1.11.2]heneicosane-20-propanoic acid, 2,2,4,4-tetramethyl-21-oxo-, tetradecyl ester), (7-oxa-3,20-diazadispiro[5.1.11.2]heneicosan-21-one, 2,2,4,4-tetramethyl-20-(oxiranylmethyl)-), (propanamide, N-(2,2,6,6-tetramethyl-4-piperidinyl)-3-[(2,2,6,6-tetramethyl-4-piperidinyl)amino]-) (1,3-propanediamine, N,N'''-1,2-ethanediylbis-, polymer with 2,4,6-trichloro-1,3,5-triazine, reaction products with N-butyl-2,2,6,6-tetramethyl-4-piperidinamine) (CAS No. 136504-96-6), 1,1'-ethylenebis(3,3,5,5-tetramethyl-2-piperazinone), (piperazinone, 1,1',1''-[1,3,5-triazine-2,4,6-triyltris-[(cyclohexylimino)-2,1-ethanediyl]]tris[3,3,5,5-tetramethyl-), (7-oxa-3,20-diazadispiro[5.1.11.2]-heneicosane-20-propanoic acid, 2,2,4,4-tetramethyl-21-oxo-, dodecyl ester), 1,1-bis(1,2,2,6,6-pentamethyl-4-piperidyloxycarbonyl)-2-(4-methoxyphenyl)ethene, (2-propenoic acid, 2-methyl-, methyl ester, polymer with 2,2,6,6-tetramethyl-4-piperidinyl 2-propenoate) (CAS No. 154636-12-1), (propanamide, 2-methyl-N-(2,2,6,6-tetramethyl-4-piperidinyl)-2-[(2,2,6,6-tetramethyl-4-piperidinyl)amino]-), (D-glucitol, 1,3:2,4-bis-O-(2,2,6,6-tetramethyl-4-piperidinylidene)-) (CAS No. 99473-08-2), N,N'-bis(2,2,6,6-tetramethyl-4-piperidinyl) isophthalamide, 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, 1-(4-tert-butyl-2-butenyl)-4-hydroxy-2,2,6,6-tetramethylpiperidine, 4-stearoyloxy-2,2,6,6-tetramethylpiperidin, 1-ethyl-4-salicyloyloxy-2,2,6,6-tetramethylpiperidine 4-methacryloyloxy-1,2,2,6,6-pentamethylpiperidine, 1,2,2,6,6-pentamethylpiperidin-4-yl β-(3,5-ditert-butyl-4-hydroxyphenyl) propionate, 1-benzyl-2,2,6,6-tetramethyl-4-piperidinyl maleate, (di-2,2,6,6-tetramethylpiperidin-4-yl) adipate, (di-2,2,6,6-tetramethylpiperidin-4-yl)sebacate, (di-1,2,3,3,6-tetramethyl-2,6-diethylpiperidin-4-yl)sebacate, (di-1-allyl-2,2,6,6-tetramethylpiperidin-4-yl)phthalate, 1-propargyl-4-β-cyanoethyl-oxy-2,2,6,6-tetramethylpiperidine, 1-acetyl-2,2,6,6-tetramethylpiperidin-4-yl acetate, trimellitic acid tri(2,2,6,6-tetramethylpiperidin-4-yl) ester, 1-acryloyl-4-benzyloxy-2,2,6,6-tetramethylpiperidine, dibutyl-malonic acid di(1,2,2,6,6-pentamethylpiperidin-4-yl) ester, butyl(3,5-di-tert-butyl-4-hydroxybenzyl)malonic acid di(1,2,2,6,6-pentamethylpiperidin-4-yl) ester, dibenzylmalonic acid di(1,2,2,6,6-pentamethylpiperidin-4-yl) ester, dibenzylmalonic acid di(1,2,3,6-tetramethyl-2,6-diethylpiperidin-4-yl) ester, hexane-1',6'-bis-(4-carbamoyloxy-1-n-butyl-2,2,6,6-tetramethylpiperidine), toluene-2',4'-bis(4-carbamoyloxy-1-n-propyl-2,2,6,6-tetramethylpiperidine), dimethyl-bis(2,2,6,6-tetramethylpiperidine-4-oxy)silane, phenyl-tris(2,2,6,6-tetramethylpiperidine-4-oxy)silane, tris(1-propyl-2,2,6,6-tetramethylpiperidin-4-yl)phosphite, tris(1-propyl-2,2,6,6-tetramethylpiperidin-4-yl)phosphate, phenyl[bis(1,2,2,6,6-pentamethylpiperidin-4-yl)phosphonate, di(1,2,2,6,6-pentamethylpiperidin-4-yl)sebacate, N,N'-bis(2,2,6,6-tetramethylpiperidin-4-yl)hexamethylene-1,6-diamine, N,N'-bis(2,2,6,6-tetramethylpiperidin-4-yl)hexamethylene-1,6-diacetamide, 1-acetyl-4-(N-cyclohexylacetamido)-2,2,6,6-tetramethylpiperidine, 4-benzylamino-2,2,6,6-tetramethylpiperidine, N,N'-bis(2,2,6,6-tetramethylpiperidin-4-yl)-N,N'-dibutyladipamide, N,N'-bis(2,2,6,6-tetramethylpiperidin-4-yl)-N,N'-dicyclohexyl(2-hydroxypropylene), N,N'-bis(2,2,6,6-tetramethylpiperidin-4-yl)-p-xylylenediamine, 4-(bis-2-hydroxy-ethyl)amino-1,2,2,6,6-pentamethylpiperidine, 4-(3-methyl-4-hydroxy-5-tert-butyl-benz-amido)-2,2,6,6-tetramethylpiperidine, 4-methacrylamino-1,2,2,6,6-pentamethylpiperidine, 9-aza-8,8,10,10-tetramethyl-1,5-dioxaspiro[5.5]undecane, 9-aza-8,8,10,10-tetramethyl-3-ethyl-1,5-dioxaspiro[5.5]undecane, 8-aza-2,7,7,8,9,9-hexamethyl-1,4-dioxaspiro[4.5]decane, 9-aza-3-hydroxymethyl-3-ethyl-8,8,9,10,10-pentamethyl-1-5-dioxaspiro[5.5]undecane, 9-aza-3-ethyl-3-acetoxymethyl-9-acetyl-8,8,10,10-tetramethyl-1,5-dioxaspiro[5.5]undecane, 2,2,6,6-tetramethylpiperidine-4-spiro-2'-(1',3'-dioxane)-5'-spiro-5"-(1'",3"-dioxane)-2"-spiro-4"-(2'",2"',6"',6"'-tetramethylpiperidin)-3-benzoyl-1,3,8-triaza-7,7,9,9-tetra-methyl-spiro[4.5]decane-2,4-dione, 3-n-octyl-1,3,8-triaza-7,7,9,9-tetramethyl-spiro-[4.5]decane-2,4-dione, 3-allyl-1,3,8-triaza-1,7,7,9,9-pentamethyl-spiro[4.5]decane-2,4-dione, 3-glycidyl-1,3,8-triaza-7,7,8,9,9-pentamethyl-spiro[4.5]decane-2,4-dione, 2-isopropyl-7,7,9,9-tetramethyl-1-oxa-3,8-diaza-4-oxyspiro[4.5]decane, 2-butyl-7,7,9,9-tetramethyl-1-oxa-3,8-diaza-4-oxyspiro[4.5]decane, 2-isopropyl-7,7,9,9-tetramethyl-1-oxa-4,8-diaza-oxyspiro[4.5]decane, 2-butyl-7,7,9,9-tetramethyl-1-oxa-4,8-diaza-3-oxyspiro[4.5]decane, bis[β-(2,2,6,6-tetramethylpiperidino)ethyl]sebacate, α-(2,2,6,6-tetramethylpiperidino)acetic acid n-octyl ester, 1,4-bis(2,2,6,6-tetramethylpiperidino)-2-butene, N-hydroxymethyl-N'-2,2,6,6-tetramethylpiperidin-4-ylurea, N-methoxymethyl-N'-2,2,6,6-tetramethylpiperidin-4-ylurea, N-methoxymethyl-N'-n-dodecyl-N-2,2,6,6-tetramethylpiperidin-4-ylurea, O-(2,2,6,6-tetramethylpiperidin-4-yl)-N-methoxymethylurethane.

Phosphites and phosphonates, such as tris(nonylphenyl)phosphite, tris(2,4-di-tert-butylphenyl) phosphite, bis(2,4-di-tert-butylphenyl)pentaerythritol diphosphite, bis(2,6-di-tert-butyl-4-methylphenyl)pentaerythritol diphosphite, 2,2'-methylenebis(4,6-di-tert-butylphenyl)octyl phosphite, tetrakis(2,4-di-tert-butylphenyl) [1,1'-biphenyl]-4,4'-diylbisphosphonite, 2,2'-ethylidenebis (4,6-di-tert-butylphenyl) fluorophosphite, dioctadecyl pentaerythritol diphosphonite, 2-[[2,4,8,10-tetrakis(1,1-dimethyl-ethyl)dibenzo[d,f][1,3,2]dioxaphosphin-6-yl]oxy]-N, N-bis[2-[[2,4,8,10-tetrakis(1,1-dimethyl-ethyl)dibenzo[d,f] [1,3,2]dioxaphosphin-6-yl]oxy]ethyl]ethanamine (CAS No. 80410-33-9), bis(2,4-di-tert-butyl-6-methylphenyl)ethyl phosphite, 2,4,6-tri-tert-butylphenyl 2-butyl-2-ethyl-1,3-propanediol phosphite or bis(2,4-dicumylphenyl)pentaerythritol diphosphite,
hydroxylamines, such as
N,N-bis(2-carboxyethyl)hydroxylamine, N,N-bis(benzylthiomethyl)hydroxylamine, N,N-diethylhydroxylamine, etc.
secondary arylamines, such as
N-(2-naphthyl)-N-phenylamine, 2,2,4-trimethyl-1,2-dihydroquinoline polymer (CAS No. 26780-96-1), N-2-propyl-N'-phenyl-p-phenylenediamine, N-(1-naphthyl)-N-phenylamine, (benzenamine, N-phenyl-, reaction products with 2,4,4-trimethylpentene) (CAS No. 68411-46-1) or 4-(1-methyl-1-phenylethyl)-N-[4-(1-methyl-1-phenylethyl)phenyl] aniline.

Lactones and benzofuranones, such as
Irganox HP 136 (CAS No. 181314-48-7)
Thioethers and thioesters, such as
distearyl 3,3-thiodipropionate, dilauryl 3,3'-thiodipropionate, ditetradecyl thiodipropionate, di-n-octadecyl disulphide.

UV absorbers, such as
(methanone, [methylenebis(hydroxymethoxyphenylene)]bis [phenyl-), (methanone, [1,6-hexane-diylbis[oxy(2-hydroxy-4,1-phenylene)]]bis[phenyl-), 2-benzoyl-5-methoxyphenol, 2,4-dihydroxybenzophenone, 2,2'-dihydroxy-4-methoxybenzophenone, 2-hydroxy-4-octyloxybenzophenone, 2-hydroxy-4-dodecyloxybenzophenone, 2-(2-hydroxy-4-hexyloxyphenyl)-4,6-diphenyl-1,3,5-triazine, 2,4-bis(2,4-dimethylphenyl)-6-(2-hydroxy-4-octyloxyphenyl)-1,3,5-triazine, 2-ethoxy-2'-ethyloxalic acid bisanilide, N-(5-tert-butyl-2-ethoxyphenyl)-N'-(2-ethylphenyl)oxamide, dimethyl(p-methoxybenzylidene)malonate, 2,2'-(1,4-phenylene)bis[3,1-benzoxazin-4-one], N'-(4-ethoxycarbonylphenyl)-N-methyl-N-phenylformamidine, 4-methoxycinnamic acid 2-ethylhexyl ester, 4-methoxycinnamic acid isoamyl ester, 2-phenylbenzimidazole-5-sulphonic acid, 2-cyano-3,3-diphenylacrylic acid 2-ethylhexyl ester, 2-ethylhexyl salicylate or 3-(4-methylbenzylidene)bornan-2-one, Chelators, such as
ethylenediaminetetraacetate (EDTA), ethylenediamine, acetylacetone, nitrotriacetic acid, ethylene glycol bis(β-aminoethyl ether)-N,N-tetraacetic acid, 2,2'-bipyridine, 4,4'-dimethyl-2,2'-bipyridine, 2,2',6',2''-terpyridine, 4,4'-diphenyl-2,2'-bipyridine, 2,2'-bipyridine-3,3'-diol, 1,10-phenanthroline, 4-methyl-1,10-phenanthroline, 5-methyl-1, 10-phenanthroline, 4,7-dimethyl-1,10-phenanthroline, 5,6-dimethyl-1,10-phenanthroline, 3,4,7,8-tetramethyl-1,10-phenanthroline, 4,7-diphenyl-1,10-phenanthroline, 2,4,7,9-tetramethyl-1,10-phenanthroline, N,N,N',N'-tetramethylethylenediamine, 2-hydroxyquinoline, 8-hydroxyquinoline, 2-hydroxy-4-methylquinaldine, 5-chloro-8-hydroxyquinoline, 5,7-dichloro-8-hydroxyquinoline, 2,4-quinolinediol, 2-quinolinethiol, 8-quinolinethiol, 8-aminoquinoline, 2,2'-biquinoline, 2-quinoxalinol, 3-methyl-2-quinoxalinol, 2,3-dihydroxyquinoxaline, 2-mercaptopyridine, 2-dimethylaminopyridine, 1,2-bis(dimethylphosphino)ethane, 1,2-bis(diphenylphosphino)ethane, 1,3-bis(diphenylphosphino)propane, 1,4-bis(diphenylphosphino)butane, polyaspartic acid or iminodisuccinate.

Iodine-containing compounds, more particularly biocides, are degraded in particular in the presence of the dryers described in more detail above. Although the strongest effects are observed in the presence of these dryers, a series of further paint components also have a destabilizing effect on iodine-containing compounds, more particularly biocides. These include organic and inorganic pigments, fillers, anti-skinning agents, rheological additives such as, for example, anti-settling agents and thixotropic agents, further compounds, particularly biocides such as fungicides, bactericides, anti-fouling agents and algicides, solvents, process additives, plasticizers, UV stabilizers and heat stabilizers, corrosion inhibitors, etc. The nitrogen-containing inorganic carrier materials of the invention also display a strongly stabilizing effect here.

The compositions of the invention, used in oxidatively drying binder preparations, and the binder preparations of the invention themselves exhibit a significant reduction in drying time as compared with unstabilized iodine-containing systems, particularly systems containing IPBC or no increase in drying time as compared with the systems not equipped with IPBC (known as blank formulations).

Without the applicant wishing to state this as a scientific certainty, it is presumably the case that the mechanism which takes place is different from the removal of metal ions, as described, for example, with polymers of aziridines for the removal of heavy metal ions from wastewaters in DE-A1-19627909. Removal of heavy metal ions would diminish the activity of the siccatives employed for this purpose, and would therefore prolong the drying time accordingly.

The binder formulations of the invention are used preferably as coating materials, more particularly as paints, varnishes, primers, impregnating systems and stains. Accordingly, the invention also provides for the use of the binder formulations of the invention as coating materials.

The invention further provides for the use of the composition of the invention for protecting industrial materials against destruction or infestation by microorganisms.

The compositions of the invention are suitable for protecting industrial materials. Industrial materials in the present context are non-living materials which have been prepared for use in industry. The industrial materials are, for example, adhesives, sizes, paper and cardboard, textiles, leather, wood, wood-based materials, coating materials and plastics articles, cooling lubricants and other materials which may be infested or decomposed by microorganisms.

Examples of microorganisms which may bring about degradation or alteration of the industrial materials include bacteria, fungi, yeasts, algae and slime organisms. The active compounds of the invention act preferably against fungi, more particularly moulds, wood-discolouring and wood-destroying fungi (Basidiomycetes) and also against slime organisms and bacteria.

Microorganisms of the following genera may be mentioned by way of example:
Alternaria, such as Alternaria tenuis,
Aspergillus, such as Aspergillus niger,
Chaetomium, such as Chaetomium globosum,
Coniophora, such as Coniophora puetana,
Lentinus, such as Lentinus tigrinus,
Penicillium, such as Penicillium glaucum,
Polyporus, such as Polyporus versicolor,
Aureobasidium, such as Aureobasidium pullulans,
Sclerophoma, such as Sclerophoma pityophila,
Trichoderma, such as Trichoderma viride, Escherichia, such as Escherichia coli,
Pseudomonas, such as Pseudomonas aeruginosa,
Staphylococcus, such as Staphylococcus aureus.

The invention further provides industrial materials comprising at least one iodine-containing compound, in particular biocide, and at least one inorganic carrier material of the invention.

EXAMPLES

In the examples below, stability tests accelerated by storage at elevated temperature are carried out. The IPBC was assayed in all cases by HPLC.

Examples 1-5

Examples 1-5 describe the preparation of inventive nitrogen-containing inorganic carrier materials from inorganic carrier materials and nitrogen-containing compounds, and inventive compositions comprising IPBC and aforesaid carrier materials. Nitrogen contents were determined by means of combustion analysis on the Leco TruSpec CHN instrument.

Example 1

Reaction Product of Aerosil with Aziridine I

The oil phase, consisting of 9.0 g of Crosslinker CX-100 from DSM (trimethylolpropane tris[3-(2-methyl-1-aziridinyl)propionate]) and 2.5 g of Rhodiasolv® DIB from Rhodia (mixture consisting of diisobutyl adipate, diisobutyl glutarate, diisobutyl succinate) was emulsified with a solution of the emulsifier of 0.575 g Tanemul® KS from Tanatex (castor oil ethoxylate with 30 eq. EO) in 25 g of water under the action of an Ultraturrax (24 000 r*min$^{-1}$) for 10 minutes. The colourless emulsion obtained was metered into a dispersion of 27.0 g of Aerosil® 200 from Evonik (fumed silica having a BET surface area of 200 m$^2$/g and a DBP absorbency of 300 g/100 g) in 300 g of water with paddle stirring, followed by stirring for 24 hours.

The Aerosil loaded with the aziridine and Rhodiasolv DIB was isolated from the resultant dispersion by spray drying (Büchi B-290 spray dryer, pump output 45%, N$_2$ flow rate 35 l*min$^{-1}$, inlet 160° C., outlet 73° C.). This gave 33 g of a very fine, colourless solid (84% of theory).

In the elemental analysis, a nitrogen content of 2.0% was found.

For determining unreacted aziridine, 3.358 g of the above product was stirred at room temperature for 2 hours with 14.32 g of tetrahydrofuran, centrifuged at 13 000 rpm for 5 minutes and subjected to semiquantitative determination in the supernatant by means of LC-MS. The solution contained 1-10 ppm of the aziridine. Converted to the solid, this corresponds to a residual concentration of unreacted aziridine of between 4 and 43 ppm.

Example 1b 3.0 g of the product from Example 1 were admixed with 15 g of THF and stirred at room temperature for 2 days. The solid was subsequently isolated by filtration, washed twice with hexane and dried under reduced pressure. This gave 2.5 g of a white powder.

Example 2

Reaction Product of Aerosil with Aziridine II

The oil phase, consisting of 18.0 g of Crosslinker CX-100 from DSM (trimethylolpropane tris[3-(2-methyl-1-aziridinyl)propionate]) and 5.0 g of Rhodiasolv® DIB from Rhodia (mixture consisting of diisobutyl adipate, diisobutyl glutarate, diisobutyl succinate) was emulsified with a solution of the emulsifier of 1.15 g Tanemul® KS from Tanatex (castor oil ethoxylate with 30 eq. EO) in 50 g of water under the action of an Ultraturrax (24 000 r*min$^{-1}$) for 10 minutes. The colourless emulsion obtained was metered into a dispersion of 54.0 g of Aerosil® 200 from Evonik (fumed silica) in 600 g of a solution of 24 g of the dispersing assistant Mowiol® 3.85 (polyvinyl alcohol from Kuraray) in 576 g of water, with paddle stirring, followed by addition of 600 g of water and then by stirring for 24 hours.

The Aerosil loaded with the aziridine and Rhodiasolv® DIB was isolated from the resultant dispersion by filtration. Drying gave 75.4 g of a very fine, colourless solid (98% of theory).

Example 3

Inventive Solid IPBC Composition I

IPBC (90.0 g) is homogenized with 128.4 g of the nitrogen-containing inorganic carrier material from Example 2 (containing 23.2% of aziridine, so making the weight ratio of IPBC to aziridine 4:1) with addition of ceramic beads (Ø 40 mm) in a drum mixer. This gives a fine, colourless and homogeneous powder (IPBC content 41%).

Example 4

Inventive Solid IPBC Composition II

IPBC (90.0 g) is homogenized with 96.9 g of the aziridine formulation from Example 2 (containing 23.2% of aziridine, so making the weight ratio of IPBC to aziridine 3:1) with addition of ceramic beads (Ø 40 mm) in a drum mixer. This gives a fine, colourless and homogeneous powder (IPBC content 48%).

Example 5

Inventive Solid IPBC Composition III

IPBC (90.0 g) is homogenized with 128.4 g of the aziridine formulation from Example 1 (containing 23.03% of aziridine, so making the weight ratio of IPBC to aziridine 4:1) with addition of ceramic beads (Ø 40 mm) in a drum mixer. This gives a fine, colourless and homogeneous powder (IPBC content 41%).

Example 6

Inventive IPBC Composition IV as Solvent-Based Dispersion

Metered into 75.0 g of the rheological additive Worleethix® S6358 (a thixotroped alkyd resin from Worlee) with dissolver stirring (3700 r min$^{-1}$) are 8.0 g of the anti-skinning agent Antiskin® 444 (Borchers), 80 g of IPBC, 113.1 g of the inventive carrier material from Example 2 (containing 23.2% aziridine) and 225.9 g of Isopar® L (Isoparaffin from Exxon).

After the end of the addition, stirring on the dissolver is continued for 40 minutes more, and the resulting preliminary dispersion is ground finely using a bead mill.

Example 7

Use of Inventive Nitrogen-Containing Inorganic Carrier Materials in Binder Formulations The IPBC compositions from Example 3 and 4, respectively are incorporated in a typical, alkyd-based coating system (alkyd stain A) in the presence of a transition metal dryer (Co) and a metal oxide pigment (iron oxide). For the equipping of the coating system, the abovementioned compositions from Example 3 and 4, respectively, and, an IPBC concentrate containing IPBC and an aziridine in a ratio of 2:1 (see Table 1) without inorganic carrier material are used in each case.

TABLE 1

| IPBC/aziridine concentrate (reference II) | |
|---|---|
| IPBC | 30% by weight |
| Crosslinker CX-100** | 15% by weight |
| Rhodiasolv DIB* | 55% by weight |

*Mixture of diisobutyl adipate, diisobutyl glutarate, diisobutyl succinate, Rhodia.
**Trimethylolpropane-tris[3-(2-methyl-1-aziridinyl)propionate]

The formula of the alkyd stain A used is shown in Table 2.

To determine the stabilization, an accelerated ageing test is carried out. For this purpose, the equipped paint system is introduced into tightly sealing 200 ml glass bottles, with only a minimum, residual amount of air remaining in the container, and stored at 40° C. The results can be seen from Table 3.

lization of IPBC (see stains A-I and A-II), have a significantly higher stability than the unstabilized sample A-III. There is also a significant improvement relative to the IPBC sample stabilized only with aziridine, without (stain A-IV), although stain A-IV has a greater aziridine/IPBC ratio (1/2 vs. 1/3 and 1/4, respectively).

TABLE 3

Stability of IPBC in alkyd stains A (-I) to (-IV) at 40° C.

| Alkyd stain | Residual IPBC content [%], based on the initial value | | | |
|---|---|---|---|---|
| | Initial | 2 weeks | 4 weeks | 8 weeks |
| A-I | 100 | 100 | 99 | 99 |
| A-II | 100 | 100 | 99 | 98 |
| A-III[1)] | 100 | 96 | 52 | 0 |
| A-IV[2)] | 100 | 100 | 80 | 0 |
| A-V | 100 | 100 | 100 | 100 |

[1)]non-stabilized sample
[2)]aziridine stab. IPBC, without inorganic carrier material

Example 8

Use of Inventive Nitrogen-Containing Inorganic Carrier Materials in Binder Formulations The IPBC compositions from Examples 3, 4 and 5 are incorporated in a commercial high-build wood stain "alkyd stain B" (containing alkyd resin, white spirit, iron oxide pigment, dryer, butanone oxime, UV absorber and additives). To equip the coating system with 0.7% IPBC in each case, based

TABLE 2

Recipe of a pigmented alkyd-based stain

| | Ingredients | Alkyd stain A-I [%] | Alkyd stain A-II [%] | Alkyd stain A-V [%] | Alkyd stain A-III [%] (Ref. I) | Alkyd stain A-IV [%] (Ref. II) |
|---|---|---|---|---|---|---|
| Alkyd stain A | Vialkyd VAF 4349, 80 SD 60, from Cytec | 22.5 | 22.5 | 22.5 | 22.5 | 22.5 |
| | Polar solvent Texanol, from Eastman | 5.0 | 5.0 | — | 5.0 | 5.0 |
| | Polar solvent Rhodiasolv DIB from Rhodia | | | 5.0 | | |
| | Rheology additive BYK E411, from BYK | 0.4 | 0.4 | 0.4 | 0.4 | 0.4 |
| | Shellsol D60, from Shell Chemicals | 66.09 | 66.34 | 66.4 | 67.1 | 65.47 |
| | MK-Solcolor red iron oxide 130M (pigment preparation), from MK Chemicals | 4.0 | 4.0 | 0.4 | 4.0 | 4.0 |
| | Octa-Soligen® 69 (contains 6% Co), from Borchers | 0.3 | 0.3 | 03 | 0.3 | 0.3 |
| | IPBC composition from Example 3 | 1.71[1)] | — | — | — | — |
| | IPBC composition from Example 4 | — | 1.46[1)] | — | — | — |
| | Stabilizer from Example 1b | | | 1.0 | | |
| | IPBC | — | — | 0.7 | 0.7 | — |
| | IPBC/aziridine concentrate (reference II) | — | — | — | — | 2.33[1)] |

[1)]corresponds in each case to 0.7% by weight IPBC, based on the stain.

From Table 3 it is clear that the nitrogen-containing inorganic carrier materials of the invention, in terms of the stabion the stain, the compositions of Examples 3, 4 and 5 and also unstabilized IPBC are used in each case (see Table 4):

TABLE 4

| | Alkyd stain B-I | | Alkyd stain B-II |
|---|---|---|---|
| IPBC Composition from Example 3 | 1.71% by weight[1] | IPBC Composition from Example 4 | 1.46% by weight[1] |
| Alkyd stain B | 98.29% by weight | Alkyd stain B | 98.54% by weight |

| | Alkyd stain B-III | | Alkyd stain B-IV |
|---|---|---|---|
| IPBC Composition from Example 5 | 1.71% by weight[1] | IPBC unstabilized | 0.7% by weight |
| Alkyd stain B | 98.29% by weight | Alkyd stain B | 99.3% by weight |

[1])corresponding in each case to 0.7% by weight IPBC, based on stain

The high-build stains under investigation, each equipped with 0.7% IPBC (alkyd stain B-I to alkyd stain B-IV), were prepared by mixing the weight fractions of the alkyd stain B as indicated in Table 4 and also the stated IPBC-containing compositions.

For determining the stabilization, an accelerated ageing test is carried out. For this purpose, the equipped paint system is introduced into tightly sealing 200 ml glass bottles, with only a minimum, residual amount of air remaining in the container, and stored at 40° C. The results can be seen from Table 5, whereby only the alkyd stains B-I to B-III, equipped in accordance with the invention, exhibit no significant degradation of the IPBC after 4 weeks of storage at 40° C. For the alkyd stains I and II a good stability of IPBC is found even after 8 weeks of storage at 40° C.

TABLE 5

Stability of IPBC in alkyd stains B (-I) to (-V) at 40° C.

| | Residual IPBC content [%], based on the initial value | | | |
|---|---|---|---|---|
| Alkyd stain B | Initial | 2 weeks | 4 weeks | 8 weeks |
| I | 100 | 97 | 93 | 88 |
| II | 100 | 94 | 92 | 80 |
| III | 100 | 100 | 96 | |
| IV[1]) | 100 | 33 | 0 | 0 |

[1])non-stabilized sample

Examples 9a to 9f

In Examples 9a to 9f, the preparation is described of inventive nitrogen-containing inorganic carrier materials from inorganic carrier materials and nitrogen-containing compounds which are not aziridines, and of inventive compositions comprising IPBC and aforesaid carrier materials. Nitrogen contents were again determined by means of combustion analysis on the Leco TruSpec CHN instrument.

Example 9a

Aerosil with Lupasol FG

The oil phase consisting of 14 g of Lupasol FOG from BASF (cationic polyethylenimine with branched spherical structure/CAS No. 9002-98-6/molecular weight approximately 800 g/mol) and 3.89 g of Rhodiasolv® DIB from Rhodia (mixture consisting of diisobutyl adipate, diisobutyl glutarate, diisobutyl succinate) was emulsified with a solution of the emulsifier of 0.89 g Tanemul® KS from Tanatex (castor oil ethoxylate with 30 eq. EO) in 29.1 g of water under the action of an Ultraturrax (24 000 r*min$^{-1}$) for 10 minutes. The pale yellow emulsion obtained was added to a dispersion of 27.0 g of Aerosil® 200 from Evonik (fumed silica) in 600 g of water and stirred at room temperature for 14 hours.

The Aerosil loaded with the Lupasol PG and Rhodiasolv DIB was isolated from the resultant dispersion by spray drying (Büchi B-290 spray dryer, pump output 45-50%, N$_2$ flow rate 45 l*min$^{-1}$, inlet 160° C., outlet 73° C.). This gave 42.71 g of a very fine, colourless solid (93.3% of theory). N content: 8.50%

Example 9b

Aerosil with Lupasol WF

The oil phase consisting of 14 g of Lupasol WF from BASF (cationic polyethylenimine with branched spherical structure/CAS No. 9002-98-6/molecular weight approximately 25 000 g/mol) and 3.89 g of Rhodiasolv® DIB from Rhodia (mixture consisting of diisobutyl adipate, diisobutyl glutarate, diisobutyl succinate) was mixed and emulsified with a solution of the emulsifier of 0.89 g Tanemul® KS from Tanatex (castor oil ethoxylate with 30 eq. EO) in 29.1 g of water under the action of an Ultraturrax (24 000 r*min$^{-1}$) for 10 minutes. The white emulsion obtained was added to a dispersion of 27.0 g of Aerosil® 200 from Evonik (fumed silica) in 600 g of water and stirred at room temperature for 14 hours. The dispersion was water-thin.

The Aerosil loaded with the Lupasol WF and Rhodiasolv DIB was isolated from the resultant dispersion by spray drying (Büchi B-290 spray dryer, pump output 45-50%, N$_2$ flow rate 45 l*min$^{-1}$, inlet 160° C., outlet 70° C.). This gave 37.57 g of a very fine, colourless solid (82.0% of theory). N content: 8.88%

Example 9c

Aerosil with Lupasol FG

Aerosil® 200 (27 g) from Evonik (fumed silica) was suspended by stirring in 591 g of water. Added to this suspension with stirring is a solution of 11.9 g of Lupasol FG from BASF (cationic polyethylenimine with branched spherical structure/CAS No. 9002-98-6/molecular weight approximately 800 g/mol) in 8.1 g of water, followed by stirring at room temperature for 12 hours.

The Aerosil loaded with the Lupasol FG was isolated from the resulting dispersion by spray drying (Büchi B-290 spray dryer, pump output 45-50%, N$_2$ flow rate 45 l*min$^{-1}$, inlet 160° C., outlet 73° C.). This gave a very fine, colourless solid. N content: 8.39%

Example 9d

Aerosil with Lupasol WF

Aerosil® 200 (27 g) from Evonik (fumed silica) was suspended by stirring in 591 g of water. Added to this suspension with stirring is a solution of 11.9 g of Lupasol WF from BASF (cationic polyethylenimine with branched spherical structure/CAS No. 9002-98-6/molecular weight approximately 25 000 g/mol) in 8.1 g of water, followed by stirring at room temperature for 12 hours.

The Aerosil loaded with the Lupasol WF was isolated from the resulting dispersion by spray drying (Büchi B-290 spray dryer, pump output 45-50%, $N_2$ flow rate 45 l*min$^{-1}$, inlet 160° C., outlet 73° C.). This gave a very fine, colourless solid. N content: 7.79%

Example 9e

Aerosil with Alpamin N41

The oil phase consisting of 14 g of Alpamin N41 from Arkema (2-[(1-methyl-propyl)amino]ethanol, CAS No. 35265-04-4) and 3.89 g of Rhodiasolv® DIB from Rhodia (mixture consisting of diisobutyl adipate, diisobutyl glutarate, diisobutyl succinate) was emulsified with a solution of the emulsifier of 0.89 g Tanemul® KS from Tanatex (castor oil ethoxylate with 30 eq. EO) in 29.1 g of water under the action of an Ultraturrax (24 000 r*min$^{-1}$) for 10 minutes. The pale yellow emulsion obtained was added to a dispersion of 27.0 g of Aerosil® 200 from Evonik (fumed silica) in 600 g of water and stirred at room temperature for 14 hours.

The Aerosil loaded with the Alpamin N41 and Rhodiasolv DIB was isolated from the resultant dispersion by spray drying (Büchi B-290 spray dryer, pump output 55%, $N_2$ flow rate 45 l/min, inlet 160° C., outlet 57-61° C.). This gave 31.22 g of a very fine, colourless solid (68.2% of theory). N content: 1.15%

Example 9f

Aerosil with Alpamin N41

Aerosil® 200 (27 g) from Evonik (fumed silica) was suspended by stirring in 591 g of water. Added to this suspension with stirring is a solution of 11.9 g of Alpamin N41 from Arkema (2-[(1-methylpropyl)amino]ethanol, CAS No. 35265-04-4) in 8.1 g of water, followed by stirring at room temperature for 12 hours.

The Aerosil loaded with the Alpamin N41 was isolated from the resulting dispersion by spray drying (Büchi B-290 spray dryer, pump output 55%, $N_2$ flow rate 45 l/min, inlet 160° C., outlet 43-61° C.). This gave 26.36 g of a very fine, colourless solid (67.8% of theory). N content: 1.17%

Example 10

Use of the Nitrogen-Containing Inorganic Carrier Materials of Examples 9a to 9f in Binder Formulations The nitrogen-containing inorganic carrier materials from Examples 9a to 9f are incorporated in a typical, alkyd-based coating system (alkyd stain A) in the presence of a transition metal dryer (Co) and a metal oxide pigment (iron oxide).

The formula for the alkyd stain A used is shown in Table 6.

To determine the stabilization, an accelerated ageing test is performed. For this purpose, the equipped paint system is introduced into tightly sealing 200 ml glass bottles, with only a minimal residual amount of air remaining in the container, and stored at 40° C. The results can be seen in Table 7.

TABLE 6

Formula of a pigmented, alkyd-based stain

| | Ingredients | Alkyd stain A-VI [%] | Alkyd stain A-VII [%] | Alkyd stain A-VIII [%] | Alkyd stain A-IX [%] | Alkyd stain A-X [%] | Alkyd stain A-XI [%] |
|---|---|---|---|---|---|---|---|
| Alkyd stain A | Vialkyd VAF 4349, 80 SD 60, Cytec | 22.5 | 22.5 | 22.5 | 22.5 | 22.5 | 22.5 |
| | Polar solvent Rhodiasolv DIB Rhodia | 5.0 | 5.0 | 5.0 | 5.0 | 5.0 | 5.0 |
| | Rheology additive BYK E411, BYK | 0.4 | 0.4 | 0.4 | 0.4 | 0.4 | 0.4 |
| | Shellsol D60, Shell Chemicals | 66.4 | 66.4 | 66.4 | 66.4 | 66.4 | 66.4 |
| | MK-Solcolor red iron oxide 130M (pigment preparation), MK Chemicals | 0.4 | 0.4 | 0.4 | 0.4 | 0.4 | 0.4 |
| | Octa-Soligen® 69 (contains 6% Co), Borchers | 0.3 | 0.3 | 0.3 | 0.3 | 0.3 | 0.3 |
| | IPBC | 0.7 | 0.7 | 0.7 | 0.7 | 0.7 | 0.7 |
| | Stabilizer from Example 9a | 0.77 | — | — | — | — | — |
| | Stabilizer from Example 9b | — | 0.77 | — | — | — | — |
| | Stabilizer from Example 9c | — | — | 0.77 | — | — | — |
| | Stabilizer from Example 9d | — | — | — | 0.77 | — | — |
| | Stabilizer from Example 9e | — | — | — | — | 0.77 | — |
| | Stabilizer from Example 9f | — | — | — | — | — | 0.77 |

TABLE 7

Stability of the IPBC in alkyd stains A-VI to A-XI at 40° C.

| Alkyd stain | Residual IPBC content [%], relative to the starting value | | | |
|---|---|---|---|---|
| | Start | 2 weeks | 4 weeks | 8 weeks |
| A-VI | 100 | 100 | | |
| A-VII | 100 | 100 | | |
| A-VIII | 100 | 100 | | |
| A-IX | 100 | 100 | | |
| A-X | 100 | 100 | | |
| A-XI | 100 | 100 | | |

What is claimed is:

1. A processes for stabilizing iodine-containing compounds, the process comprising:
adding a nitrogen-containing inorganic carrier material to an iodine-containing compound, wherein:
the nitrogen-containing inorganic carrier material comprises at least one nitrogen-containing compound adsorptively or covalently bonded to an inorganic carrier material; and
the iodine containing compound is selected from the group consisting of diiodomethyl p-tolysulphone, diiodomethyl p-chlorophenyl sulphone, 3-bromo-2-3-diiodo-2-propenyl alcohol, 2,3,3-triiodoallyl alcohol, 4-chloro-2-(2-chloro-2-methylpropyl)-5-[(6-iodo-3-pyridinyl)methoxy]-3(2H)-pyridazinone (CAS RN: 120955-77-3), iodofenfos, 3-iodo-2-propynyl 2,4,5-trichlorophenyl ether, 3-iodo-2-propynyl-4-chlorophenyl formal (IPCF), N-iodopropargyloxycarbonylalainine, ethyl N-iodopropargyloxycarbonylalanine, 3-(3-iodopropargyl)benzoxazol-2-one, 3-(3-iodo-propargyl)-6-chlorobenzoxazol-2-one, 3-iodo-2-propynyl alcohol, 4-chlorophenyl-3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

2. The process according to claim 1, wherein the nitrogen-containing compound is selected from the following:
A) compounds of the formula (Ia)

R¹R²R³N        (Ia)

in which
R¹, R² and R³ each independently of one another are hydrogen, alkyl, alkenyl or aryl or in pairs together form a 3- to 7-membered N-heterocyclic, aliphatic, unsaturated or aromatic ring,
the radicals alkyl, alkenyl or aryl or the 3- to 7-membered N-heterocyclic, aliphatic, unsaturated or aromatic ring being either unsubstituted or substituted one or more times by radicals selected from the group consisting of hydroxyl, fluoro, chloro, bromo, Iode, carboxyl, alkylsulphonyl, arylsulphonyl, nitrile and isonitrile,
but at least one of the radicals R¹, R² and R³ is not hydrogen
B) polyamines, and
C) aziridines.

3. The process according to claim 2, wherein the nitrogen-containing inorganic carrier material has a nitrogen content of 0.01% to 10% by weight.

4. The process according to claim 3, wherein the inorganic carrier material is selected from the group consisting of silica, fumed silicas, diatomite, porosils, clathrasils, dealuminated zeolites, aluminosilicates, zeolites, natural or synthetic tectosilicates, natural silicates, mica, and pyrogenic metal oxides.

5. The process according to claim 1, wherein:
the iodine containing compound is 3-iodo-2-propynyl butylcarbamate (IPBC);
the nitrogen-containing compound is selected from:
A) compounds of the formula (Ia)

R¹R²R³N        (Ia)

in which
R¹, R² and R³ each independently of one another are hydrogen, alkyl, alkenyl or aryl or in pairs together form a to 7-membered N-heterocyclic, aliphatic, unsaturated or aromatic ring,
the radicals allyl, alkenyl or aryl or the 3- to 7-membered N-hetero-cyclic, aliphatic, unsaturated or aromatic ring being either unsubstituted or substituted one or more times by radicals selected from the group consisting of hydroxyl, fluoro, chloro, bromo, iodo, carboxyl, alkylsulphonyl, arylsulphonyl, nitrile and isonitrile,
but at least one of the radicals R¹, R² and R³ is not hydrogen
B) polyamines, and
C) aziridines; and
the inorganic carrier material is selected from the group consisting of silica, fumed silicas, diatomite, porosils, clathrasils, dealuminated zeolites, aluminosilicates, zeolites, natural or synthetic tectosilicates, natural silicates, mica or pyrogenic metal oxides.

6. A composition comprising:
a) at least one nitrogen-containing inorganic carrier material comprising at least one nitrogen-containing compound adsorptively or covalently bonded to an inorganic carrier material; and
b) at least one iodine-containing compound selected from the group consisting of diiodomethyl p-tolysulphone, diiodomethyl p-chlorophenyl sulphone, 3-bromo-2,3-diiodo-2-propenyl alcohol, 2,3,3-triiodoallyl alcohol, 4-chloro-2-(2-chloro-2-methylpropyl)-5-[(6-iodo-3-pyridinyl)methoxy]-3H(2H)-pyridazinone (CAS RN: 120955-77-3), iodofenfos, 3-iodo-2-propynyl 2,4,5-trichlorophenyl ether, 3-iodo-2-propynyl-4-chlorophenyl formal (IPCF), N-iodopropargyloxycarbonylalanine, ethyl N-iodopropargyloxycarbonylalanine, 3-(3-iodopropargyl)benzoxazol-2-one, 3-(3-iodopropargyl)-6-chlorobenzoxazol-2-one, 3-iodo-2-propynyl alcohol, 4-chlorophenyl-3-iodopropargyl formal, 3-iodo-2-propynyl propylcarbamate, 3-iodo-2-propynyl butylcarbamate (IPBC), 3-iodo-2-propynyl m-chlorophenylcarbamate, 3-iodo-2-propynyl phenylcarbamate, di(3-iodo-2-propynyl) hexyldicarbamate, 3-iodo-2-propynyloxyethanol ethylcarbamate, 3-iodo-2-propynyloxyethanol phenylcarbamate, 3-iodo-2-propynyl thioxothioethylcarbamate, 3-iodo-2-propynyl carbamate (IPC), 3-bromo-2,3-diiodo-2-propenyl ethylcarbamate, 3-iodo-2-propynyl n-hexylcarbamate and 3-iodo-2-propynyl cyclohexylcarbamate.

7. The composition according to claim 6, wherein the iodine-containing compound is 3-iodo-2-propynyl butylcarbamate (IPBC).

8. The composition according to claim 6, wherein the nitrogen-containing compound is an organic compound.

9. The composition according to claim 8, wherein the nitrogen-containing compound is selected from the following:
A) compounds of the formula (Ia)

$$R^1R^2R^3 \tag{Ia}$$

in which
$R^1$, $R^2$ and $R^3$, each independently of one another, are hydrogen, alkyl, alkenyl or aryl, or in pairs together form a 3- to 7-membered N-heterocyclic, aliphatic, unsaturated or aromatic ring,
the radicals alkyl, alkenyl or aryl, or the 3- to 7-membered N-heterocyclic, aliphatic, unsaturated or aromatic ring being either unsubstituted or substituted one or more times by radicals selected from the group consisting of hydroxyl, fluoro, chloro, bromo, iodo, carboxyl, alkylsulphonyl, arylsulphonyl, nitrile and isonitrile, and
at least one of the radicals $R^1$, $R^2$ and $R^3$ is not hydrogen,
B) polyamines, and
C) aziridines.

10. The composition according to claim 6, wherein the inorganic carrier material is selected from the group consisting of silica, fumed silicas, diatomite, porosils, clathrasils, dealuminated zeolites, aluminosilicates, zeolites, natural or synthetic tectosilicates, natural silicates, mica or pyrogenic metal oxides.

11. The composition according to claim 6, wherein:
the nitrogen-containing compound is selected from:
A) compounds of the formula (Ia)

$$R^1R^2R^3N \tag{Ia}$$

in which
$R^1$, $R^2$ and $R^3$, each independently of one another, are hydrogen, alkyl, alkenyl or aryl, or in pairs together form a 3- to 7-membered N-heterocyclic, aliphatic, unsaturated or aromatic ring,
the radicals alkyl, alkenyl or aryl or the 3- to 7-membered N-hetero-cyclic, aliphatic, unsaturated or aromatic ring being either unsubstituted or substituted one or more times by radicals selected from the group consisting of hydroxyl, fluoro, chloro, bromo, iodo, carboxyl, alkylsulphonyl, arylsulphonyl, nitrile and isonitrile, and
at least one of the radicals $R^1$, $R^2$ and $R^3$ is not hydrogen,
B) polyamines, and
C) aziridines; and
the inorganic carrier material is selected from the group consisting of silica, fumed silicas, diatomite, porosils, clathrasils, dealuminated zeolites, aluminosilicates, zeolites, natural or synthetic tectosilicates, natural silicates, mica or pyrogenic metal oxides.

12. The composition according to claim 6, wherein:
the iodine-containing compound is 3-iodo-2-propynyl butylcarbamate (IPBC);
the nitrogen-containing compound is selected from:
A) compounds of the formula (Ia)

$$R^1R^2R^3N \tag{Ia}$$

in which
$R^1$, $R^2$ and $R^3$, each independently of one another, are hydrogen, alkyl, alkenyl or aryl, or in pairs together form a 3- to 7-membered N-heterocyclic, aliphatic, unsaturated or aromatic ring,
the radicals alkyl, alkenyl or aryl or the 3- to 7-membered N-hetero-cyclic, aliphatic, unsaturated or aromatic ring being either unsubstituted or substituted one or more times by radicals selected from the group consisting of hydroxyl, fluoro, chloro, bromo, iodo, carboxyl, alkylsulphonyl, arylsulphonyl, nitrile and isonitrile, and
at least one of the radicals $R^1$, $R^2$ and $R^3$ is not hydrogen,
B) polyamines, and
C) aziridines;
the inorganic carrier material is selected from the group consisting of silica, fumed silicas, diatomite, porosils, clathrasils, dealuminated zeolites, aluminosilicates, zeolites, natural or synthetic tectosilicates, natural silicates, mica or pyrogenic metal oxides; and
the nitrogen-containing inorganic carrier material has a nitrogen content of 0.01% to 10% by weight.

13. The composition according to claim 12, wherein the aziridines are those of the formula I

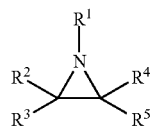

(I)

where
$R^1$ is hydrogen, alkyl or cycloalkyl, each of which are unsubstituted or substituted and/or mono- or polyethylenically unsaturated, or in each case substituted or unsubstituted fullerenyl, aryl, alkoxy, alkoxycarbonyl, arylcarbonyl, alkanoyl, carbamoyl or oxomethylene,
$R^2$, $R^3$, $R^4$ and $R^5$ independently of one another have the same definition as $R^1$ and additionally independently are halogen, hydroxyl, carboxyl, alkylsulphonyl, arylsulphfonyl, nitrile or isonitrile, or the radicals
$R^2$ and $R^4$ or $R^3$ and $R^5$, together with the carbon atoms to which they are attached, form a 5 to 10-membered carbocyclic ring which is unsubstituted or substituted and/or mono- or polyethylenically unsaturated.

14. A process for protecting industrial materials against destruction or infestation by microorganisms, the process comprising treating industrial materials with the composition according to claim 6.

15. The process according to claim 14, wherein the process comprises treating the industrial materials with the composition according to claim 7.

16. The process according to claim 14, wherein the process comprises treating the industrial materials with the composition according to claim 11.

17. An industrial material protected against destruction or infestation by microorganisms, the industrial material comprising the composition according to claim 6.

18. The industrial material according to claim 17, wherein the industrial material comprises the composition according to claim 7.

* * * * *